United States Patent
Staggs et al.

(10) Patent No.: US 11,110,035 B1
(45) Date of Patent: Sep. 7, 2021

(54) TACTICAL MEDICINE DISPENSERS

(71) Applicant: GRAM TACTICAL LLC, Nashville, TN (US)

(72) Inventors: James William Staggs, Nashville, TN (US); Scott Gordon Rhodes, Nashville, TN (US); Brian Cummings, Nashville, TN (US)

(73) Assignee: GRAM TACTICAL LLC, Nashville, TN (US)

( * ) Notice: Subject to any disclaimer, the term of this patent is extended or adjusted under 35 U.S.C. 154(b) by 33 days.

(21) Appl. No.: 15/423,919

(22) Filed: Feb. 3, 2017

Related U.S. Application Data

(60) Provisional application No. 62/291,916, filed on Feb. 5, 2016.

(51) Int. Cl.
| | | |
|---|---|---|
| A61J 7/00 | (2006.01) | |
| A61J 1/03 | (2006.01) | |
| B65D 75/36 | (2006.01) | |
| B65D 83/04 | (2006.01) | |
| A45F 5/02 | (2006.01) | |

(Continued)

(52) U.S. Cl.
CPC ............. *A61J 7/0076* (2013.01); *A45F 5/021* (2013.01); *A61J 1/03* (2013.01); *A61J 1/035* (2013.01); *A61K 9/0056* (2013.01); *A61K 9/20* (2013.01); *A61K 31/40* (2013.01); *A61K 31/44* (2013.01); *A61K 31/46* (2013.01); *A61K 31/5513* (2013.01); *B65D 75/366* (2013.01); *B65D 83/04* (2013.01); *A61J 2200/30* (2013.01)

(58) Field of Classification Search
CPC . A61J 7/0076; A61J 1/03; A61J 1/035; A61K 9/0056; A61K 9/20; B65D 83/04; B65D 75/366; A45F 5/021
USPC ........... 206/536, 528, 531, 534, 38, 37, 807, 206/459.1, 459.5; 221/22, 23, 190, 287, 221/191, 25, 30, 31, 69
See application file for complete search history.

(56) References Cited

U.S. PATENT DOCUMENTS 4,078,660 A * 3/1978 Lerro ..................... A44C 5/003
128/897
4,753,377 A * 6/1988 Poluhowich ......... A44B 11/005
2/338

(Continued)

OTHER PUBLICATIONS

Liang et al., "Fast-dissolving intraoral drug delivery systems," Expert Opinion on Therapeutic Patents, 11(6):981-986 (2001) (abstract).

*Primary Examiner* — Rafael A Ortiz

(57) ABSTRACT

A portable medicament case that includes a medicament provided in a package, and first and second housing members that are configured to form a medicament package receiving cavity when joined together. Each housing member including a mating member that is configured for engagement with the other housing member in order to join the first and second housing members together in a sealed configuration that prevents moisture or contaminants from entering into the cavity. Also, a magazine containing a plurality of medicament cases for administration of medicaments to a group of people, and a method of administering medications to mass casualties of multiple persons that are in need thereof. The medicaments are rapidly disintegratable and can include a dye that stains the person's mouth so that medical personnel can determine who has been treated with the medicament.

20 Claims, 18 Drawing Sheets

(51) Int. Cl.
  *A61K 9/00* (2006.01)
  *A61K 9/20* (2006.01)
  *A61K 31/46* (2006.01)
  *A61K 31/44* (2006.01)
  *A61K 31/40* (2006.01)
  *A61K 31/5513* (2006.01)

(56) References Cited

U.S. PATENT DOCUMENTS

| | | | |
|---|---|---|---|
| 4,946,684 A | 8/1990 | Blank et al. | |
| 5,178,298 A | 1/1993 | Allina | |
| 5,269,413 A * | 12/1993 | Stern | B65D 51/26 |
| | | | 206/37 |
| 5,460,295 A | 10/1995 | Law | |
| 5,576,014 A | 11/1996 | Mizumoto et al. | |
| 5,882,116 A * | 3/1999 | Backus | B65D 55/06 |
| | | | 383/5 |
| 5,915,560 A | 6/1999 | George et al. | |
| 6,200,604 B1 | 3/2001 | Pather et al. | |
| 6,316,026 B1 | 11/2001 | Tatara et al. | |
| 6,316,029 B1 | 11/2001 | Jain et al. | |
| 6,543,639 B1 | 4/2003 | Kovens | |
| 7,062,312 B2 | 6/2006 | Gonzales et al. | |
| 7,214,385 B2 | 5/2007 | Gruber | |
| 7,264,136 B2 | 9/2007 | Willoughby et al. | |
| 8,016,157 B2 * | 9/2011 | Norris | B65D 83/049 |
| | | | 221/286 |
| 8,517,236 B2 | 8/2013 | Kushner | |
| 8,906,413 B2 | 12/2014 | Chang et al. | |
| 2002/0076437 A1 | 6/2002 | Kothari et al. | |
| 2003/0230498 A1 * | 12/2003 | Maute | A61J 1/03 |
| | | | 206/38 |
| 2004/0265375 A1 | 12/2004 | Platteeuw et al. | |
| 2005/0232988 A1 | 10/2005 | Venkatesh et al. | |
| 2006/0141031 A1 * | 6/2006 | Nelson | A61K 9/0056 |
| | | | 424/464 |
| 2010/0133140 A1 | 6/2010 | Bailey et al. | |
| 2010/0294692 A1 | 11/2010 | Gelardi | |
| 2011/0000931 A1 | 1/2011 | Gelardi et al. | |
| 2012/0325688 A1 * | 12/2012 | Davis | A46B 15/0061 |
| | | | 206/38 |
| 2013/0161207 A1 * | 6/2013 | Luciano, Jr. | A61J 1/03 |
| | | | 206/1.5 |
| 2013/0206801 A1 * | 8/2013 | Delgatty | A45F 5/00 |
| | | | 224/219 |
| 2014/0117060 A1 * | 5/2014 | Colone | A44C 5/003 |
| | | | 224/219 |
| 2014/0140784 A1 * | 5/2014 | Vick | F16B 2/20 |
| | | | 410/97 |
| 2014/0166523 A1 * | 6/2014 | Williams-Hartman | |
| | | | B65D 73/0035 |
| | | | 206/459.5 |

\* cited by examiner

TACTICAL MEDICINE DISPENSERS

CROSS-REFERENCE TO RELATED APPLICATIONS

This application claims the benefit of provisional application 62/291,916 filed Feb. 5, 2016, the entire content of which is expressly incorporated herein by reference thereto.

FIELD OF THE INVENTION

The present invention relates to tactical medical dispensers and medicine for use by personnel that do not have ready access to medical supplies, such as soldiers and sailors on deployment and/or in a war zone, and/or other parties under various situations, such as police or National Guard personnel handing a disturbance or disaster.

BACKGROUND OF THE INVENTION

Soldiers and sailors can find themselves in difficult circumstances. In battlefield situations, one medic may accompany a platoon of soldiers (a group typically of 20 or 25 up to about 75 soldiers). One corpsman may cover an entire ship. This medic may be carrying all of the pain medication should a trauma situation occur for any of the soldiers. Serious problems can occur if something happens to the medic or worse yet, if many soldiers are hurt at the same time. Studies have shown that Post Traumatic Stress Disorder (PTSD) has increasing adverse effects, and can be more common, with the amount of delay in initially treating a patient following a traumatic injury. If a medic is disabled, the time to administer medicaments to the soldiers can be delayed or prevented. And if soldiers are injured, delays will occur even if the medic is available to administer treatment.

Another problem relates to how the medicament is administered. Auto injectors are a group of spring loaded syringes of medicine used in the battlefield (such as to administer pain medication, ephedrine, etc.), but these devices are somewhat bulky, fragile and are advertised as being required to be kept at specific temperatures, e.g., 77° F. It will likely be very hard to maintain a specific temperature or temperature range on a battlefield. Additionally, the instructions for use recommend that the patient should be non-mobile for 45 seconds after administration of the drug. This may not be practical in a military or other mass injury scenarios.

Thus, there is a need for a fast acting pharmaceutical composition which can be administrated anywhere and anytime without liquid, which is suitable in battlefield situation or massive terrorist attacks liquids to provide an immediately perceivable therapeutic effect.

There also is a need for a better method and vehicle for carrying and dispensing medication to soldiers and sailors in battle or during conflict, as well as to handle large scale administration of medicaments in such situations. These needs are now met by the present invention.

SUMMARY OF THE INVENTION

Accordingly, the present invention has been made to provide improved tactical containers for military and/or other uses, and in particular, improved medical dispensers for individual dosage for self-medication. Additionally, a rapid dispenser for administering medication to large numbers of individuals in need is also provided.

An improved container or pod system is now provided whereby doses of medication can be quickly and effectively deployed to individuals in need. These containers can be secured to a base such as to various equipment whether that be dog tags, credit card style devices, bracelets, buckles, or connected to various other devices such as using molle connections, Alice connections, or other connection systems.

The invention specifically relates to a dynamic medication package and delivery system to handle a fast-paced, tactical environment. The single administration device is referred to as a pod and is designed to hold medication, attach on-person as a band on the wrist or clipped onto gear as a molle clip, for use in connection with the administration of medicaments to individuals or groups in a more efficient manner.

In one embodiment, the pod is designed to improve current methods for a soldier/medic to carry, apply and/or distribute necessary medicaments that are needed to be carried on-gear. It is small, waterproof, and durable, and is can be opened single-handedly, when on-the-go, for immediate access to the medicament for consumption by the person carrying it or for administration to a colleague. The pods are made to be discarded after use with the carrying base configured to allow reloading of a new pod onto base when still attached to an existing band or clips.

There are different specific configurations of these pods that can be used with two preferred constructions available for different situations. One pod has a circular design which can be opened by a twisting movement, while another one has an elongated housing resembling a military dogtag and which is opened with a sliding, drawer-like motion. Both pods are made of a military grade plastic material or metal which provides the necessary ruggedness and impact resistance as well as providing a water tight enclosure that secured the medicament therein.

The pods typically contain a medicament that is in the form of a pill, tablet, wafer or other orally consumed dosage form. A preferred medicament is one that is in the form of a dissolving tablet with specific formulations that instantly disintegrate in the oral cavity, releasing medication directly into the bloodstream through the sublingual route, taking action more quickly than injection or topical options and even faster than oral medications in the form of capsules. These tablets can contain a single medication or a blend of multiple medications that would normally be taken simultaneously and individually. The fast dissolving tablet can also be prepared to hold a greater dosage amount than currently provided by medics or other medical personnel.

Single or dual combinations of tablets or pills are preferably provided in a blister pack or other containment device that is securely retained in the pod and that prevents moisture from contacting and degrading the medicament. Any containment device must be relatively easy to open to allow quick access to the medicament therein. This can be done by providing weakened portions or score lines in the pack or containment device.

In another embodiment of the invention, the medicament includes at least one dye in an effective amount to stain a person's mouth as an identification of consuming the oral composition. The dye is present to provide a distinctive color stain when the oral composition is consumed such that a simple viewing of the person's mouth readily identifies whether the person consumed the medicament or not. This is extremely useful when medicaments are to be distributed to large numbers of people in need as it can be quickly determined who received the medication and who did not simply by visually observing the person's mouth. Also, the color can be used as an indication of the type of medicament that is distributed as a further confirmation that the correct medicament has been dispensed.

The invention also provides a device that can administer multiple dosages of the medication rapidly and effectively. This device is a magazine of many pods packaged as a unit that can be easily dispensed to mass amounts of people in a chaotic situation; such as an act of terrorism, natural or in industrial or natural disasters. The magazine can hold as little as 10 or 20 to as many as 100 pods or more for such situations. This is extremely beneficial to tactical, military situations where a large number of personnel are engaged, but it also serve a valuable, life-saving service to mass-gathering situations; such as stadiums events or on-hand for smaller, specific groups; like government bases and buildings. A single magazine or a finite number of magazines can be provided for smaller operations while several connected magazines can be provided for large stadium events and battlefield situations.

The invention also provides a feature for identifying what persons have consumed medicaments. This is particularly important when medicaments are dispensed to large numbers of people such as mass casualties from a battle or terrorist attack. The medicaments that are retained in the containers in the magazine each include a dye therein that will stain the person's mouth when consuming the medicament. This provides a visible indication that the medicament has been administered to the person. This can demonstrate quickly whether the person received treatment or not and is also an indicator to other medical personnel who may later treat the person or persons. For example, when medics initially distribute certain drugs which are appropriate (nerve gas counteractants, or even simple pain medication) to a group of soldiers who are in need of such treatment, the dye can provide a quick indicator to the medics as to who was treated (mouth is colored or stained) and who is left to be treated (no mouth stain). And after the injured are transported in an ambulance or helicopter, different medical personnel are involved and they can easily determine whether the persons have been treated. The same is true once the injured arrive at a hospital. The color indicates that the person has been treated with some pharmaceutical so that even if the injured person is now unconscious, the doctors can understand what they have taken before doing surgeries or other procedures.

The medicaments can be identified by color codes of the dye, and this also assists in making sure that the medic has distributed the correct drug. As there are not enough colors to code each type of drug with a different color, but the point would be that in a particular situation the same drug (or class of drugs, e.g., pain killers) is administered to all of the injured so whatever color is included is sufficient to provide the information as to who received the drug. Also, the coloring of certain drugs (e.g., narcotics) could also be used prevent abuse such as to prevent overdosing where the person says he was not treated but the coloration of his mouth is evidence that he was already treated.

BRIEF DESCRIPTION OF THE DRAWINGS

The present invention will be more clearly understood and readily practiced by understanding the features thereof as illustrated in the following drawing figures, wherein.

Figure 1A:
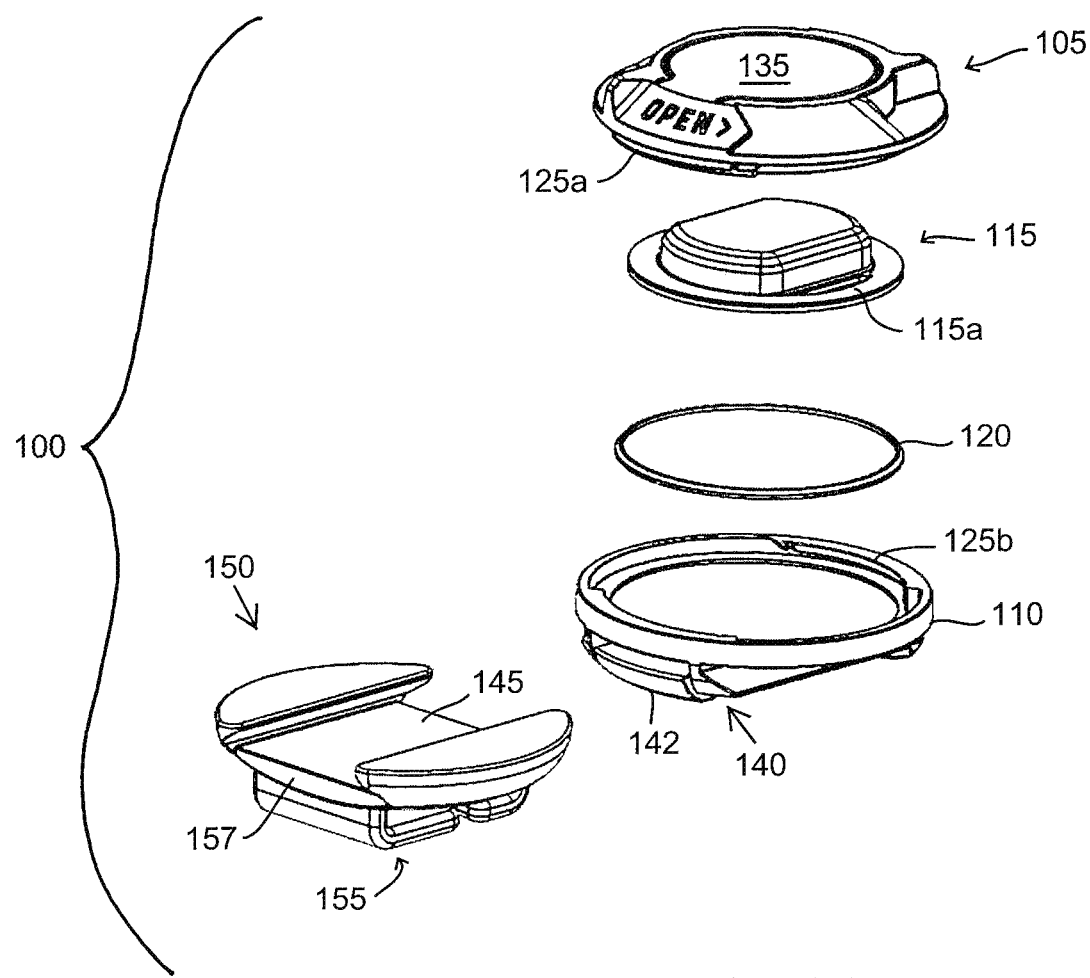
FIG. 1A is an exploded top-down perspective view of a portable medicament case in accordance with the present invention.

The components in the figures are not necessarily to scale, emphasis instead being placed upon illustrating the principles of the invention. Moreover, in the figures, like reference numerals designate corresponding parts throughout the different views. Moreover, all illustrations are intended to convey the inventive features, where relative sizes, shapes and other detailed attributes may be illustrated schematically rather than literally or precisely. The detailed description provides further details of what is shown in the drawings and discusses logical and useful alternatives thereto.

DETAILED DESCRIPTION OF THE INVENTION

The invention generally provides a portable medicament case comprising a medicament provided in a package; and first and second housing members that are configured to form a medicament package receiving cavity when joined together, with each housing member including a mating member that is configured for engagement with the other housing member in order to join the first and second housing members together in a sealed configuration that prevents moisture or contaminants from entering into the cavity. Advantageously, one housing member includes an aperture that assists in removing the medicament package from that housing member when the housing members are not joined together in the sealed configuration.

In one embodiment, the first housing member includes an exterior surface exposed to the environment and an interior surface facing the package, the interior surface defining the aperture and including an adhering member for retaining the package is located in the interior surface of the first housing member; and an ejection button associated with the aperture and configured to disengage the package from the first housing member upon depression by application of finger force that overcomes the adhering member when the housing members are not joined together in the sealed configuration. The adhering member preferably includes a pair of rib members which extend into the cavity about the medicament package to secure the medicament package to the first housing member, and wherein the package includes openings to engage with the rib members.

The medicament package is a blister pack that is sealed to further prevent moisture from contacting the medicament. The medicament package may also be a container that is sealed to prevent moisture from entering but that is relatively easy to open. The blister packs generally include a weakened membrane of plastic or metal foil that the medicament can break through and open with finger force. The container can have screw treads or a snap-locking cap, or it can be provided with a weakened area or line that allows quick access to the medicament.

The portable medicament case can further comprise a gasket located between the first and second housing members to provide a hermetic seal about the medicament package when the housing members are in the mating engagement in the sealed configuration.

To remove the medicament package, the ejection button has a shape and dimension that conforms to that of the aperture of the first housing member, each of the ejection button and the aperture having a thickness and parameter that provides a snug fit of the ejection button in the first housing aperture but allows depression of the ejection button by finger force into the cavity. The ejection button can instead form part of the first housing member by a portion of the ejection button directly connected to a sidewall or upper surface of the first housing member.

The second housing member may be operatively associated with a base member that includes means for connection that forms or is connectable to a rod, strap, belt or clothing article for secure transport of the portable medicament case on or with a person. In particular, a lower portion of the second housing member has a ramp member that has angled sidewalls and an upper portion of the base member has a slot with angled sidewalls that are complimentary to those of the ramp member so that the ramp member can be slid into and securely received by the slot.

The mating members of the portable medicament case comprise threads that are engaged by screwing the first housing member onto the second housing member, and wherein the first housing member further comprises opening members configured as a wall member that protrudes from a floor of the first housing member and that is engageable by a user's hand to provide a twisting force to the first housing member for disengagement from the second housing member. Preferably, the opening members are operatively associated with the threaded mating members to allow rotation of the first housing member in only one rotation direction.

In another embodiment, the first housing member of the portable medicament case is an elongated male slide member having upper, lower and side walls and a forward end that includes the aperture therein, and the second housing member is an elongated female member having a rearward end that has upper, lower and side walls and that forms a closed cavity that is configured for receiving the forward end of the slide member therein.

The first housing member further comprises a rearward end that includes a grasping portion for removing the slide member from the cavity, the grasping portion including arm members that are attached to the forward end, and the second housing member lower wall includes a rearward end that has an opening therein that snugly receives the medicament package therein such that when the slide member is withdrawn from the cavity and placed over that opening, the medicament package can be removed by depressing an upper portion of the medicament package using finger force to remove the medicament package from the aperture.

The lower wall member of the rearward portion of the first housing member preferably includes a slot and a terminal barrier at a forward end of the slot, and the rearward end of the second housing member includes a protrusion that travels in the slot as the first housing member is withdrawn from the cavity of the second housing member but that contacts the terminal barrier at the forward end of the slot to position the aperture of the first housing member above the opening of the second housing member and to also prevent complete disengagement of the first housing member from the second housing member.

For any of the embodiments disclosed herein, the medicament (a) comprises an oral composition that comprises at least one active pharmaceutical ingredient in a therapeutically effective amount and at least one dye in an effective amount to stain a person's mouth as an identification of consuming the oral composition, or (b) is formulated with one or more disintegrating agents configured to rapidly disintegrate when placed in a person's mouth, or (c) is a formulation that includes both (a) and (b). The medicament is advantageously in a tablet or wafer dosage form comprising one or more appropriate excipients or diluents formulated with the active pharmaceutical ingredient and the dye.

In one arrangement, the medicament includes sufficient dye to temporarily stain at least the person's tongue and mouth and optionally stain the person's teeth and lips upon consumption of the oral composition when the oral composition contacts the person's saliva. Alternatively, the medicament may be formulated to dissolve in the person's mouth in less than 45 seconds, less than 30 seconds, or less than 15 seconds.

The medicament can be any one of an analgesic agent, a sedative, an antibiotic, or an antidote to a chemical agent. The chemical agent may be a nerve agent which is selected from the group consisting of soman, sarin, tabun, cyclosarin, GV, a novichock agent, EA-3148, VE, VG, VM, VP, VR, VX, Trilon-83, saxitoxin, and a combination thereof. The antidote to a chemical agent may be selected from the group consisting of atropine sulfate, 2-PAM, diazepam, procyclidine, and a combination thereof.

FIG. 1A depicts a first embodiment of a portable medicament case 100 in accordance with the present invention. The case 100 comprises a first housing member 105, a second housing member 110, and a medicament package 115. The first housing member 105 and the second housing member 110 are configured to form a medicament package receiving cavity when joined together. Each housing member may include a mating member 125*a*, 125*b* that is configured for engagement with the other housing member in order to join the first and second house members 105, 110 together in a manner that prevents moisture or contaminants from entering into the cavity. The mating members 125*a*, 125*b* may comprise threads that are engaged by screwing the first housing member 105 onto the second housing member 110 or vice versa. The first housing can also include indicia to indicate the direction of rotation for disengagement from the second housing.

The first housing member 105 generally includes an exterior surface and an interior surface. The exterior surface may be exposed to the environment whereas the interior surface is in contact with the package 115. The interior surface may define an aperture 130 and include an adhering member, and the package 115 may be inserted into the aperture 130 and secured to the adhering member. In one embodiment, the adhering member may include a pair of rib members 122 that extend toward the medicament package 115 or the second housing member 110. The rib members 122 may be engaged with the openings 115a of the package 115 to hold the package 115 against the first housing member 105. In another embodiment, the adhering member may include an adhesive that attaches the package 115 to the first housing member 105. The aperture 130 may form part of the cavity when the housing members 105, 110 are joined together. The first and second housings are made of a plastic or elastomeric material, with an engineering thermoplastic material that has impact and moisture resistant properties being preferred.

The first housing member 105 may include an ejection button 135 that is configured to be pushed toward the package 115 (or the second housing member 110) to loosen the package 115 from the second housing member 110. Whether the ribs or an adhesive are used, the joining force is one that is weak and that can be overcome by finger force to disengage the package 115 from the first housing 105. When the adhering member includes a pair of rib members 122, the depression causes the rib members 122 to become disengaged from the openings 115a on the package 115. Disengagement in this situation may refer to that the rib members 122 not being in physical contact with the opening 115a or the package 115, or that the rib members 122 are moved to a position such that the package 115 can be removed from the rib members 122.

When the adhering member includes an adhesive, the adhesive is one that exhibits a force sufficient to weakly attach the package 115 to the first housing member 105 so the package 115 does not fall out of the first housing member 105 when it is disengaged from the second housing member 110. The force is also weak enough to be broken by the application of by finger force so the package 115 may be removed from the first housing member 105 when access to the medicament is needed. The button 135 may have one side on the exterior surface and another side on the interior surface. The button 135 or the side of the button 135 that is on the interior surface may define part of the aperture or reside at least partially within the aperture.

The ejection button can be configured to be retained in the aperture by frictional force, whereas the outer circumference of the button is essentially the same size and the inner circumference of the aperture. The frictional engagement is sufficient to maintain the button in the aperture but with such a low force that the button can be pushed out of the aperture by finger force when the housings are separated and the person desires to access the medicament. The button can be made of the same plastic material as the housing members but often the button can be made of a softer thermoplastic or elastomeric material so that it can be more easily fit into and removed from the surrounding aperture. Making the button of a softer material also facilitates sealing the button in the aperture to prevent moisture from entering into the cavity between the housings by wicking past the button.

When the package 115 is secured to the first housing member 105, the first housing member 105 including the package 115 may be engaged (e.g., screwed) onto the second housing member 110 to seal the package 115. The package 115 is accessible by disengaging (e.g., unscrewing) the first housing member 105 from the second housing member 110 and pushing the button 135 toward the package 115 to release the package 115 from the first housing member 105. The case 100 may also comprise a gasket 120 located between the housing members 105, 110 to provide a hermetic seal about the package 115 when the housing members 105, 110 are joined together through the mating members 125a, 125b. Preferably, the gasket 120 is located between the package 115 and the second housing member 110. The gasket 120 may have a circular shape or other shape. When the gasket 120 has a circular shape, it may have a circumference that is larger than or at least the same size as the circumference of the package 115. The gasket 120 may cover the entire bottom portion of the package 115 so that no region on the bottom portion is exposed to the second housing member 110. The gasket 120 may be a flexible or rigid mechanical seal.

The package 115 may include a medicament and may be a blister pack that is sealed to prevent moisture from contacting the medicament. The package 115 may include one or more openings 115a to be secured to the adhering member of the first housing member 105. The package 115 may include a base and a shield protruding from the base. The base may be made of aluminum foil or similar material that can be opened by finger force. The shield may be transparent for viewing the medicament and be made of plastic. The openings 115a may be located on the base.

Figure 1B:
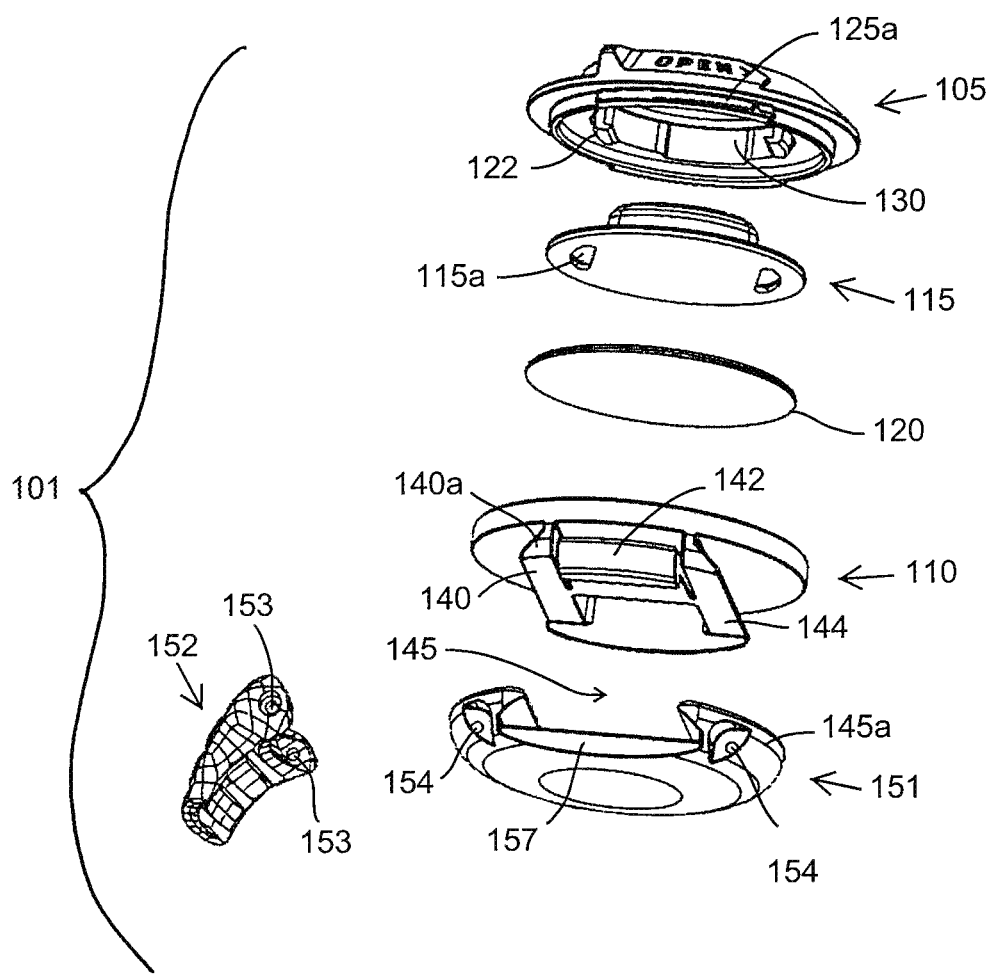
FIG. 1B is an exploded bottom-up perspective view of another portable medical case which is similar to that of FIG. 1A but which has a different base connection.

The second housing member 110 may be operatively associated with a base member 150 that includes means 155 for connection to a rod, strap, belt, band, clothing article, bandolier, or other article for secure transport of the case 100 on or with a person. These articles can be worn on the user's wrist or body. The second housing member 110 may include a first surface configured to receive the first housing member 105 and a second surface opposite to the first surface having a ramp member 140. The mating member 125b of the second housing member 110 may be located on the first surface. The ramp member 140 may include angled sidewalls 140a as shown in FIG. 1B. The base member 150 may include an upper portion having a slot 145 with angled sidewalls 145a and a bottom portion having the means 155 for connection. The angled sidewalls 145a of the slot 145 are preferably complimentary to the angled sidewalls 140a of the ramp member 140 so that the ramp member 140 can be slid into and received by the slot 145. The ramp member 140 may have a varying thickness in the cross-sectional view that widens towards the base member 150.

Similarly, the slot 145 may have an opening that widens towards the means 155 for connection and the opening may have a trapezoid-shaped cross section. When the ramp member 140 is in the slot 145, the case 100 cannot be removed from the base member 150 in any direction except in the sliding direction. The ramp member 140 may include a clip 142 to fix the second housing member or the case 100 to the base member 150. The second housing member or the case 100 can be fixed to the base member 150 via the clip 142 once the ramp member 140 is slid into the slot 145. The base member 150 may include a lip 157 for engaging the clip 142. The lip 157 may extend from one of the angled sidewalls 145a toward the other one of the angled sidewalls 145a of the slot 145 of FIG. 1B. In one embodiment, the ramp member 140 may include a pair of legs 144 with each having an angled sidewall 140a. The thickness of each leg 144 in the cross-sectional view may widen toward the base member 150. The legs 144 may be parallel to each other and the clip 142 may extend from one leg to the other.

In FIG. 1A, the means for connection 155 may include a pair of L-shaped elements. One of the L-shaped elements may be attached to one end of the slot 145 and the other one of the L-shaped elements may be attached to another end of the slot 145. The ends of the slot 145 refer to the ends that the ramp member 140 can enter into or exit from the slot. The L-shaped members may be attached the ends in a manner such that they extend toward each other. The lip 157 may be formed on one of the ends. The L-shaped elements may form a first opening for receiving an article and a second opening for accommodating the received article that has a size larger than the first opening.

The article may be a rod, strap, belt, band, clothing article, bandolier, or other article for secure transport of the case 100 on or with a person. The article may be configured to be worn on the user's wrist or body or carried by the user. The user may be a person responsible for distributing the medicament or a person who may consume the medicament. The L-shaped elements may be constructed from flexible materials. When the base member 150 (or the base member 150 having the case 100) is installed on the article, the base member 150 may be slidable along the article. The sliding direction along the article may be perpendicular to the sliding direction of the ramp member 140 along the slot 145.

FIG. 1B illustrates similar embodiment of a medicament case but one which has a different connection to the base 151. Components of FIG. 1B that are the same as those of FIG. 1A are shown with the same numerals. A watch band, schematically shown as 152, can be connected to openings 154 on the base 151. In this way, the portable medicament case can be worn in the same manner as a watch.

Figure 2A:
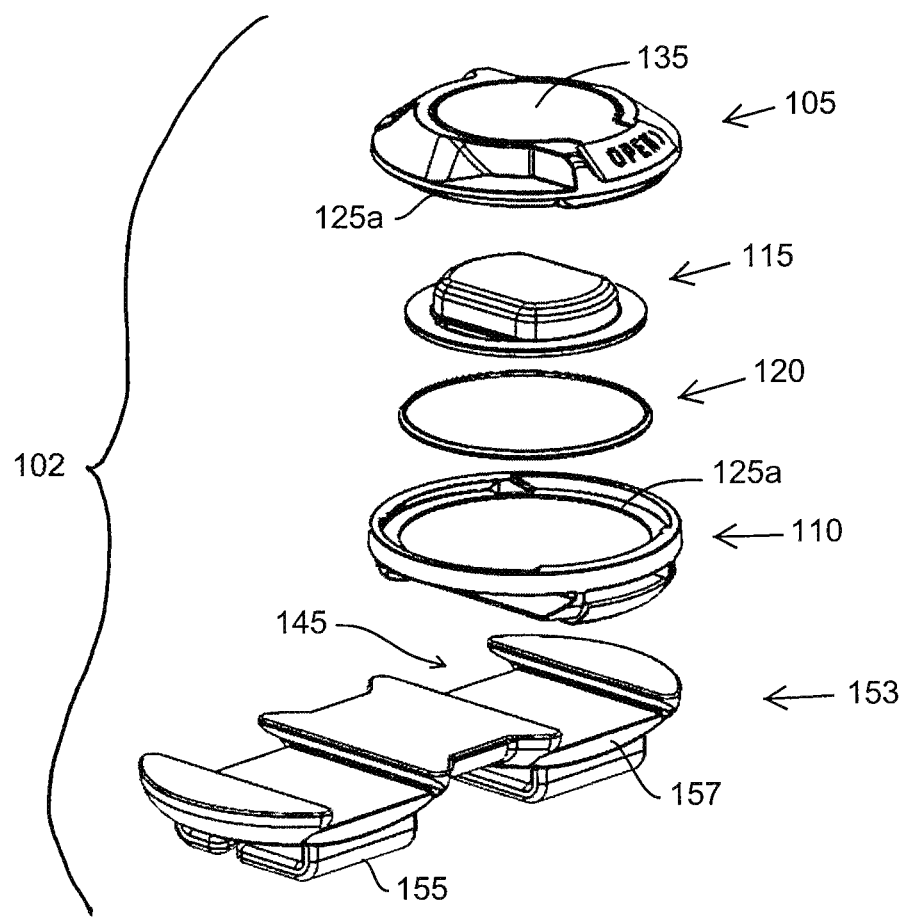
FIG. 2A is an exploded top-down perspective view of another embodiment of a portable medicament case of the present invention.
Figure 2B:
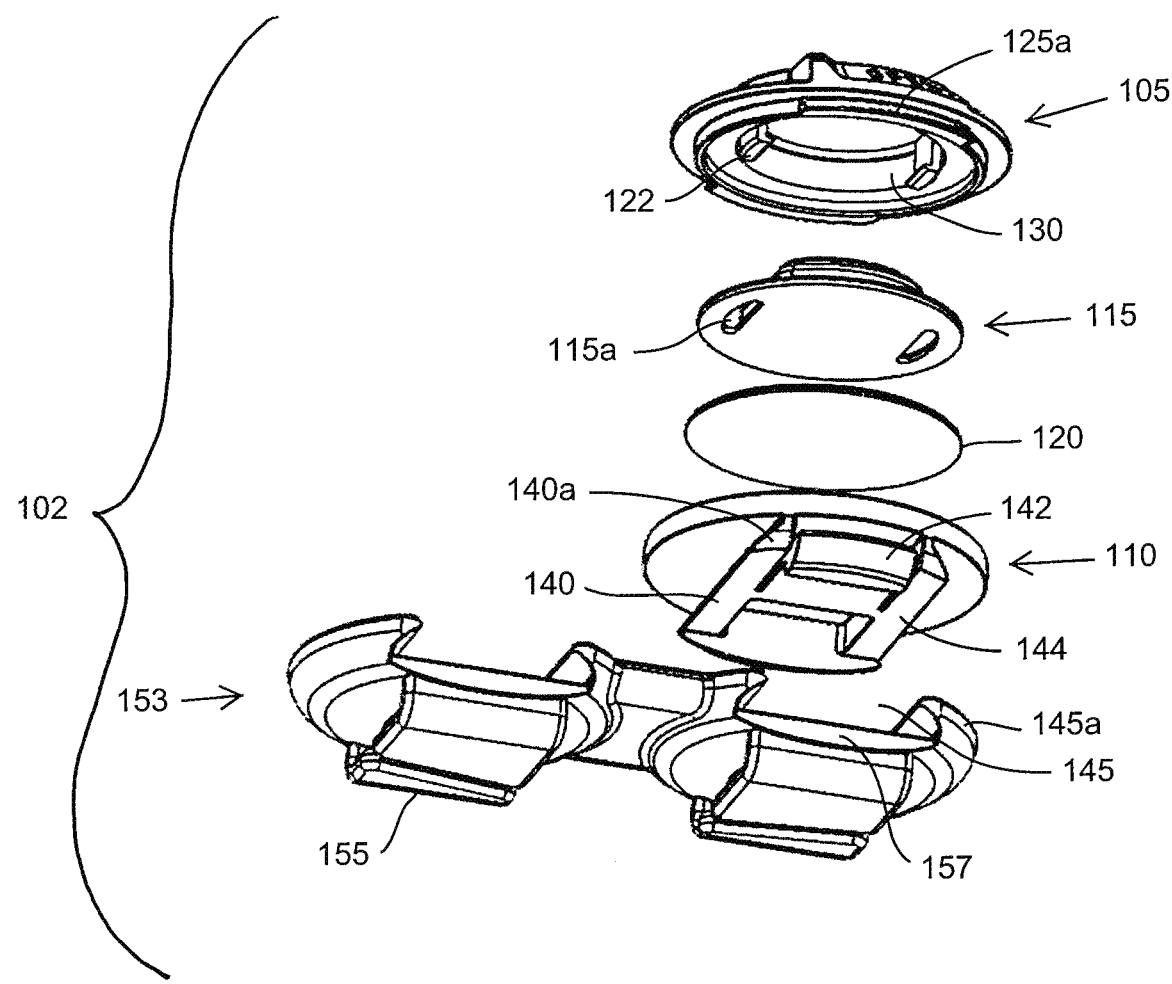
FIG. 2B is an exploded bottom-up perspective view of the portable medicament case of FIG. 2A.

The base member 150 may be configured to be a single-case mount (as shown in FIG. 1A), a double-case mount 153 (as shown in FIGS. 2A and 2B), or as a multiple-case mount and may be secured to the article to be worn or carried by the user whether it is a single-, double-, or multiple-case mount. The multiple case mount can include 3, 5, 10 or more cases. For smaller mounts, the article may be an item similar to a watch strap and the base member 150 may be a single-case mount attached to the watch strap such that the case 100 may be worn like a watch. The base member 153 is a double-case mount as shown in FIGS. 2A and 2B wherein that article may be worn on the wrist or on a leg.

When the user needs to bring a number of cases that is more than the maximum number of cases that can be worn on the wrist, the user may wear a belt, bandolier, or other longer band to carry multiple cases. Such belt, bandolier, and other longer band may also be used to carry a single-case mount if desired. When the base member 153 is configured to be a double-case mount or a multiple-case mount, the base member 153 may not need to include means 155 for connection under each slot. For example, the means 155 for connection may be provided under every other slot or under other slots. The number of cases to be applied to the belt, band, rod or strap is not limited. While an individual may carry only a small number of 1 to 5 cases on his wrist or belt, the larger numbers of cases, up to 10 or even more, may be carried on some type of support for use by medical personnel to administer the medicament to larger numbers of people in need, such as the victims of a terrorist act or a natural disaster, as well as to soldiers who are injured in a military engagement.

The first housing member 105 may also be referred to as the upper housing member and the second housing member 110 may also be referred to as the lower housing member when their positions are measured from the base member 150 or 153. The difference between FIGS. 1A and 2A/2B is that FIG. 1A depicts a base member 150 with single-case mount whereas FIGS. 2A/2B depict a base member 153 with double-case mount. All the other details are identical.

Figure 3A:
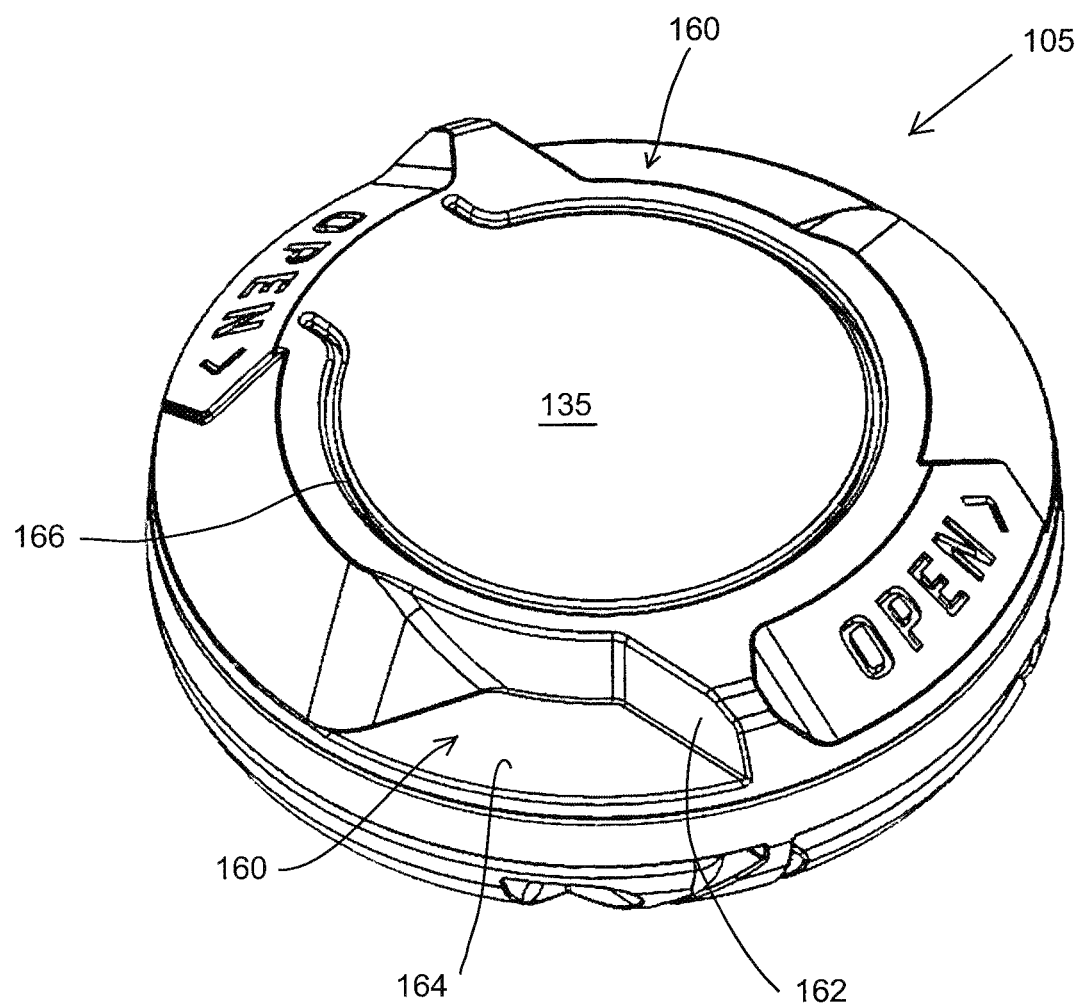
FIG. 3A is a detailed top view of the exterior surface of a first housing member for the portable medicament case of FIGS. 1A, 1B, 2A and 2B.

FIG. 3A depicts a detailed view of the exterior surface of the first housing member 105 in accordance with some embodiments of the present invention. As discussed above, the first housing member 105 includes an ejection button 135 and the button 135 may form part of the exterior surface of the first housing member 105. FIG. 3A also depicts a top view of the case 100 or the first housing member 105 mated to the second housing member.

The exterior surface of the first housing member 105 may further include opening members 160 with each configured as a wall member 162 that protrudes from a floor 164 of the first housing member 105. The wall member 162, or the combination of the wall member 162 and the floor 164, may be engageable by a user's hand to provide a twisting force to the first housing member 105 for disengagement from the second housing member. The configuration of the wall members provides a grip which is formed as a notch in the first housing.

The wall members are preferably configured and oriented to facilitate rotation in only one direction. Alternatively, if desired, a different type of locking can be provided between the first and second housings so that the notch can be configured to allow access to the medicaments by rotation of the first housing in either direction with respect to the second housing. This can be achieved by a slotted interlocking arrangement between the housings whereas rotation by an angle of 30 to 45 degrees in either direction allows the housings to be separated. The one way configuration for rotation is preferred as it results in a more secure screw connection between the housings that is less likely to be accidentally opened.

The button 135 may be formed on the top of the wall member 162 and be parallel to the floor 164. The button 135 may be a piece of rigid structure that is connected to the wall member 162 via a flexible structure 166 that enables the button 135 to be depressed. The button 135 and the structure 166 both may also be flexible structures to provide this movement. The structure 166 may be made of rubber or other materials having similar physical characteristics to provide the necessary elasticity and a complete hermetic seal for the medicament package underneath the first housing member 105. The button 135 may be separated from the other parts of the first housing member 105 by the structure 166. The button 135 may be partially surrounded by the structure 166 with only a portion of the perimeter of the button 135 directly connected a sidewall of the first housing member 105. The remaining portion of the perimeter may be connected to the sidewall via the structure 166.

In one embodiment, the structure 166 may be a ring of rubber surrounding the button 135 with an opening allowing the button 135 to be connected to the sidewall (e.g., a C-shaped ring). The button 135 may be depressed to release the package when the first housing member 105 is disengaged from the second housing member. Before the disengagement, the button 135 may be depressed but the depression may not release the package from the first housing member 105 because the movement of the interior surface, the adhering member, and/or other structures caused by the depression is limited due to the engagement. In some embodiments, however, the button 135 may be depressed to release the package onto the second housing member before the first housing member 105 is disengaged from the second housing member. Therefore, the user may push the button 135 first to release the package and then disengage the first housing member to retrieve the package on the second housing member.

In some embodiments, the first housing member 105 and the button 135 may configured such that, when the button 135 is depressed, the button 135 or the first housing member 105 pushes the medicament through the base of the package and causes the medicament to land on the second housing member 110. Therefore, when the first housing member 105 is disengaged from the second housing member 110, only the medicament is in the second housing member 110 and the package without the medicament remains attached to the first housing member 105.

Figure 3B:
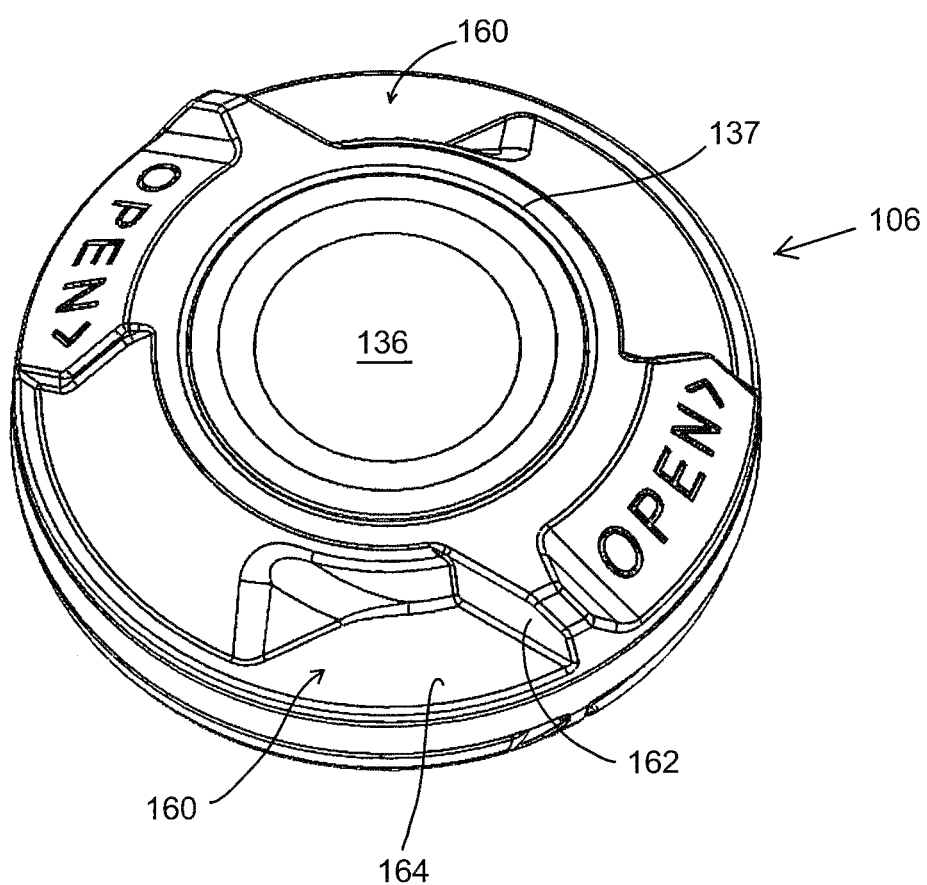
FIG. 3B is a detailed top view of the exterior surface of a first housing member which is a variant of that of FIG. 3A.
Figure 3C:
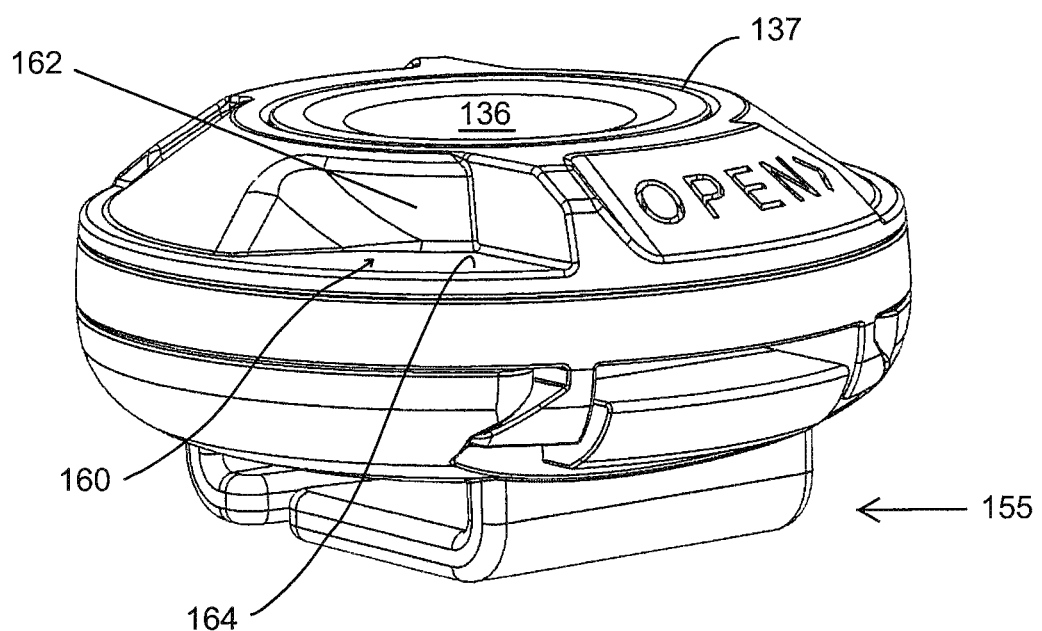
FIG. 3C is a perspective view of another embodiment of a portable medicament case that includes the first housing member of FIG. 3B.
Figure 3D:
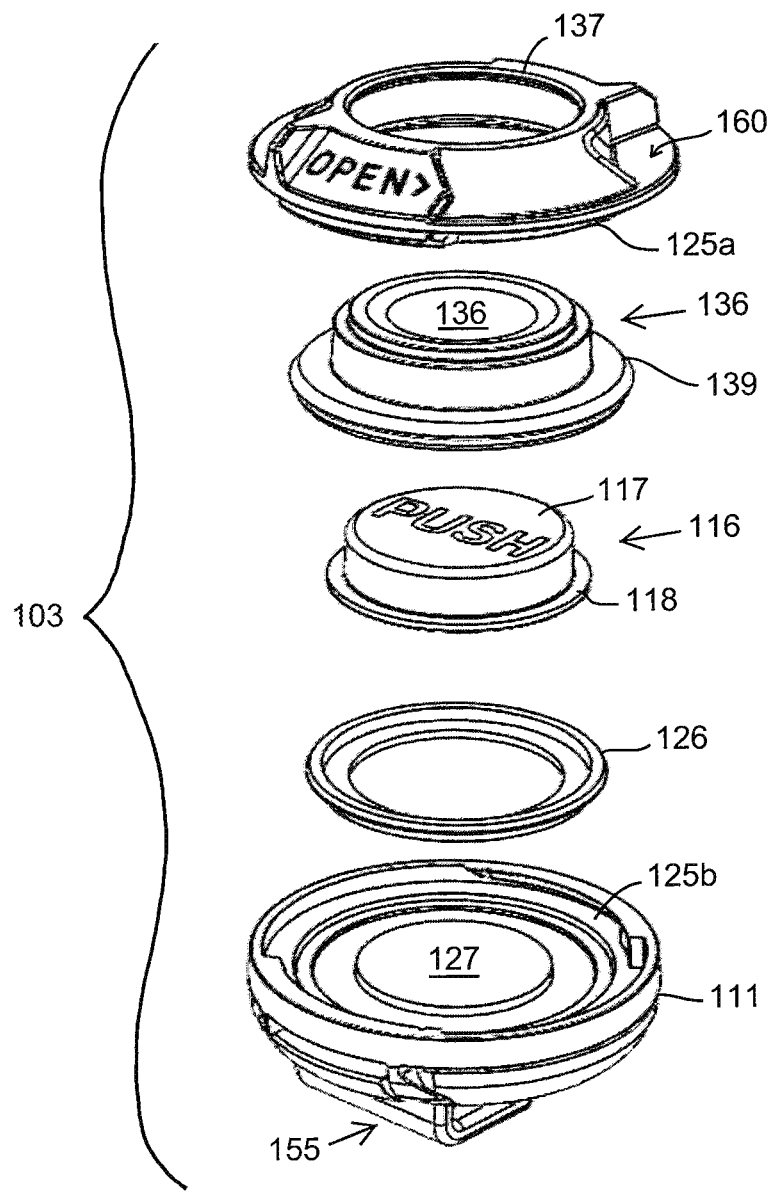
FIG. 3D is an exploded view of the portable medicament case of FIG. 3C.

In another embodiment, a related portable medicament case 103 is illustrated in FIGS. 3B, 3C and 3D. As best shown in FIG. 3B, the button 136 is not an extension from the sidewall of the first housing member 106. Instead, the button 136 is a separate component inserted into the first housing member 106. The first housing member 106 includes a hole 137 having a shape and dimension corresponding to the shape and dimension of the button 136. For example, the button 136 may be cylindrical and the hole 137 may be circular, and each may have a thickness and a circumference that provides a snug fit of the button 136 in the hole 137. Further details of this embodiment are shown in FIGS. 3C and 3D. When the same components are disclosed as in FIGS. 1A, 1B, 2 and 3A, the same element numbering is used in FIGS. 3B, 3C and 3D.

A portion or top surface 138 of the button 136 may protrude from the top surface of the first housing member 106 and a portion 139 of the button 136 may extend into the cavity. The portion 139 extending into the cavity may be in the form of a flange alone or in combination with an O-ring or gasket (not shown) to provide a hermetic seal between the button flange portion 139 and the first housing member 106 and to avoid the button 136 from falling out of the hole 137 (in the direction away from the second housing member) when the case is turned up-side down. The button 136 may include a cylindrical surface (e.g., the circumference or parameter) contacting the inner surface of the hole 137 or first housing member 106 and the surface may exhibit sufficient friction that can hold the button 136 in the hole 137 of the first housing member 106 without the button 136 falling into or away from the cavity of course provided that the frictional engagement does not hinder the movement of the button 136 when pushed by finger force.

The medicament package 116 may also be a blister package as in the other embodiments, or if desired it can be in the form of a chamber that can hold other medicaments therein. The top surface 117 of the medicament package 116 may include indicia, such as PUSH, to indicate where the user needs to apply force to open the medicament package to access the medicaments therein. And like the button 136, the medicament package can include a flange 118 to assist in properly seating the medicament package in the button 136. An O-ring or gasket (not shown) can be included to provide a hermetic seal between the medicament package flange 118 and the button flange 139, if desired, when the medicament package 116 is not otherwise sealed.

In FIGS. 3C and 3D, the second housing member 111 is illustrated. While this housing member has the same type of threaded opening 125b to mate with 125a of the first housing member, it has a different lower structure than that of the other second housing members disclosed herein. The lower structure includes L-shaped connection means 155 that are configured for engaging a strap or band so that the case can be carried by a user by securing the band to the user's wrist or leg. The band may be one piece that is expandable or configured like a belt with two ends that can be joined together.

A seal member 126 is provided to seal the first and second housing members together. This member is made of plastic or rubber having sufficient resiliency to be compressed when the two housing members are in contact, as when screwing the two housing members together. The seal member is seated in the second housing member 111 by engaging a raised disc-like structure 127 which both locates and holds the seal from movement in the second housing member 111.

In some embodiments, the first housing member 105 of FIG. 3A may include a linking mechanism (e.g., a chain or cord) to connect the button 135 to the first housing member 105. Before the button 135 is pushed, the button 135 may or may not be in contact with the package 115. When the button 135 is pushed, the button 135 contacts the package 115 and exerts an amount of force enough to disengage or separate the package from the adhering member.

Figure 4:
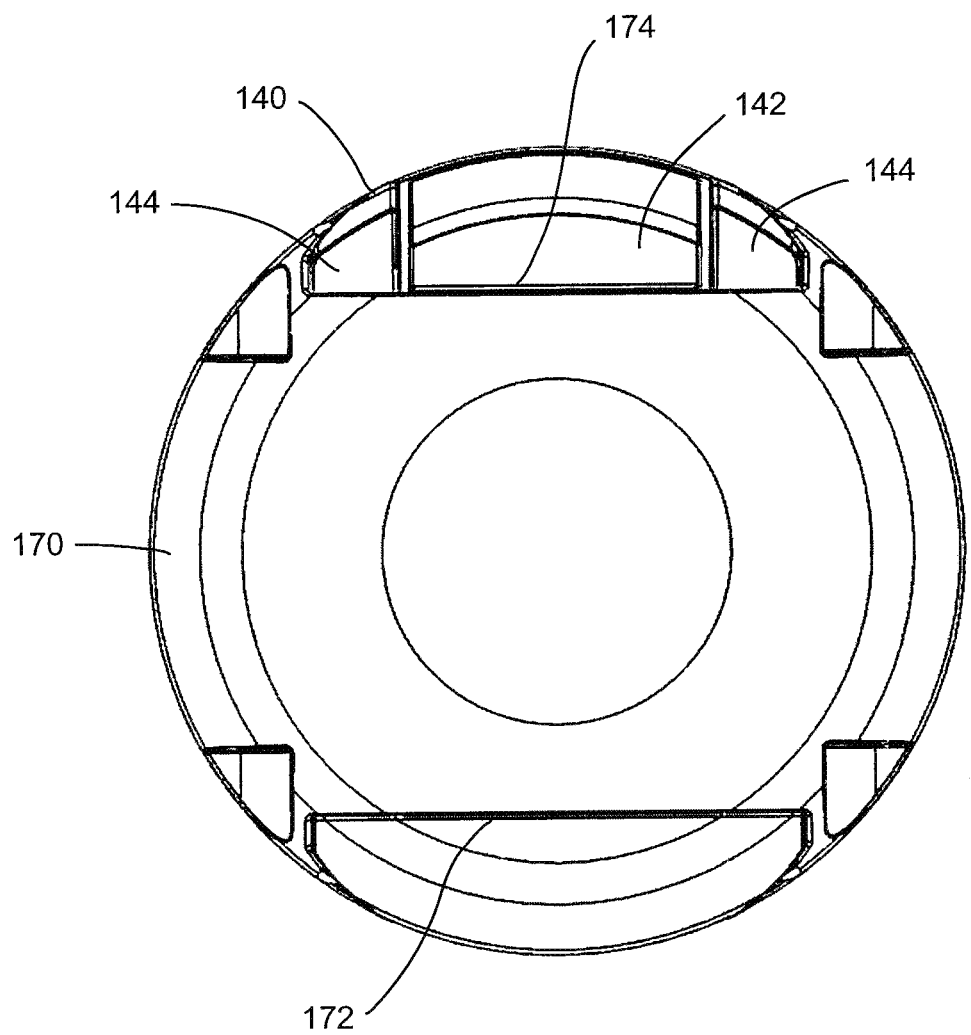
FIG. 4 is a bottom view of the portable medicament case of FIG. 1A.

FIG. 4 depicts a bottom view of the portable medicament case 100 slid into another embodiment of the base member in accordance with some embodiments of the present invention. The base member 170, like the base member 150 in FIGS. 1 and 2, may also include a slot having an end 172 and another end 174 through which the ramp member 140 can enter into or exit from the slot. The ramp member may include a pair of parallel legs 144 and a clip 142 that extends one leg to the other.

Figure 5:
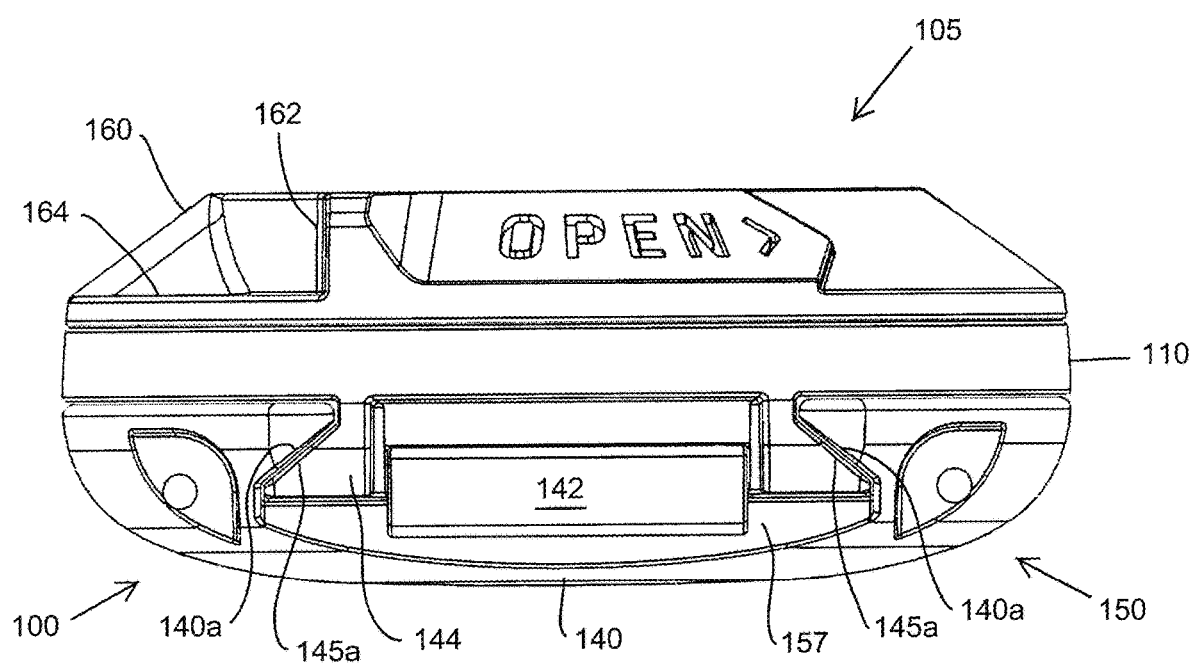
FIG. 5 is a side view the portable medicament case of FIG. 1A.

FIG. 5 depicts a side view of the portable medicament case 100 slid into the base member 150 in accordance with some embodiments of the present invention. As discussed above, the case 100 may comprise a first housing member 105 and a second housing member 110. FIG. 5 also illustrates that the first housing member 105 and the second housing member 110 are engaged. The first housing member 105 may include an opening member 160 configured as a wall member 162 that protrudes from a floor 164 of the first housing member 105.

The first housing member 105 may also include another opening member on the other side of the first housing member 105. The opening members allow the user's hand to twist the first housing member 105 for disengagement from the second housing member 110 even when the case 100 is secured to the base member 150.

The second housing member 110 may include a ramp member 140 (circled region) having angled sidewalls 140a. The base member 150 may include an upper portion having a slot with angled sidewalls 145a and a bottom portion having the means 155 for connection. The angled sidewalls 145a of the slot are complimentary to the angled sidewalls 140a of the ramp member 140.

The ramp member 140 may also include a pair of parallel legs 144 with each having an angled sidewall 140a. The ramp member 140 may also include a clip 142 that extends between the legs 144 and is engaged to the lip 157 of the base member 150 to secure the case 100 to the base member 150. FIG. 5 also illustrates that the L-shaped element of the means 155 for connection extending or curving into the page.

Figure 6A:
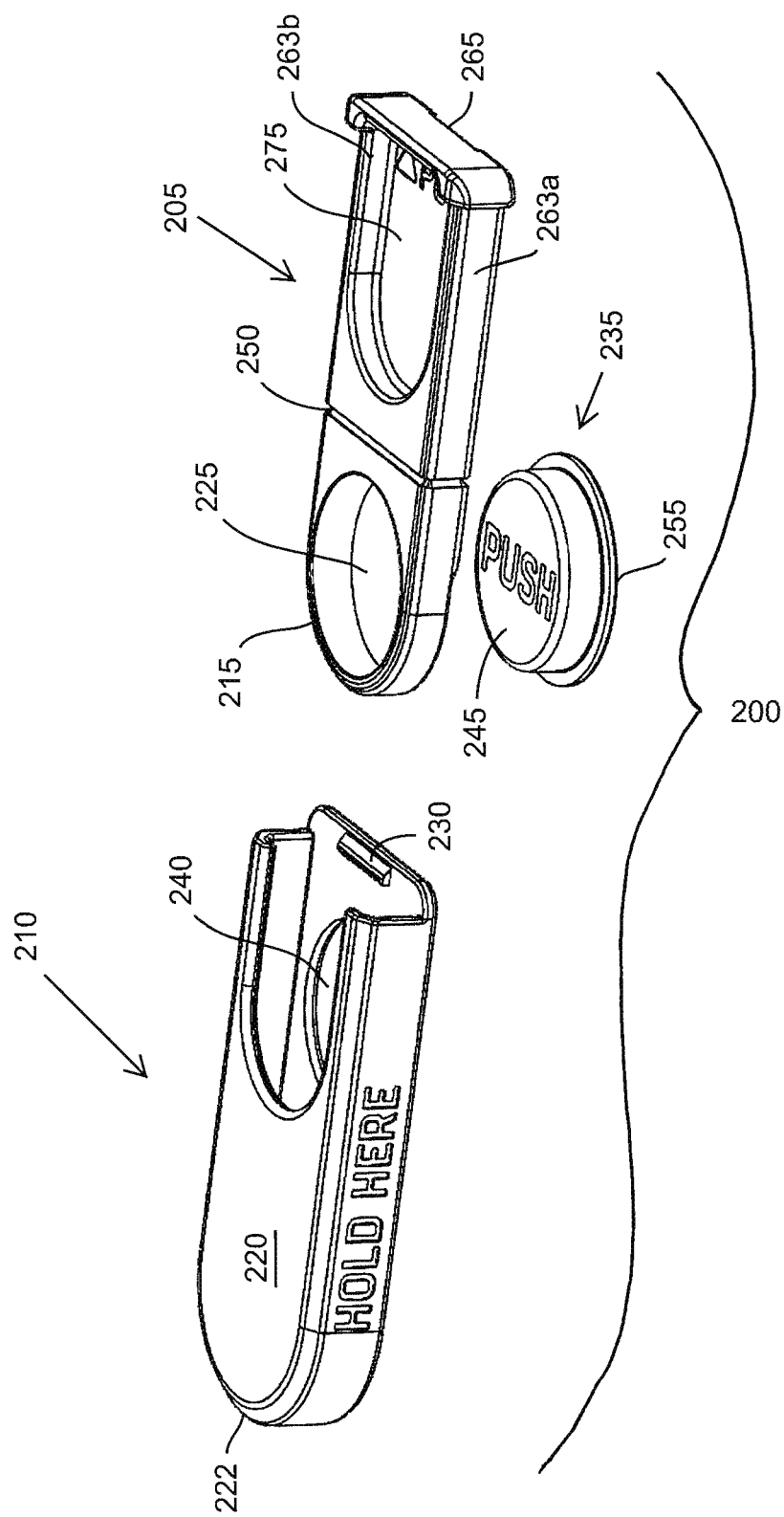
FIGS. 6A, 6B and 6C are exploded perspective views of another embodiment of a portable medicament case with FIGS. 6A and 6B being top-down perspective views and FIG. 6C being a bottom-up perspective view.
Figure 6B:
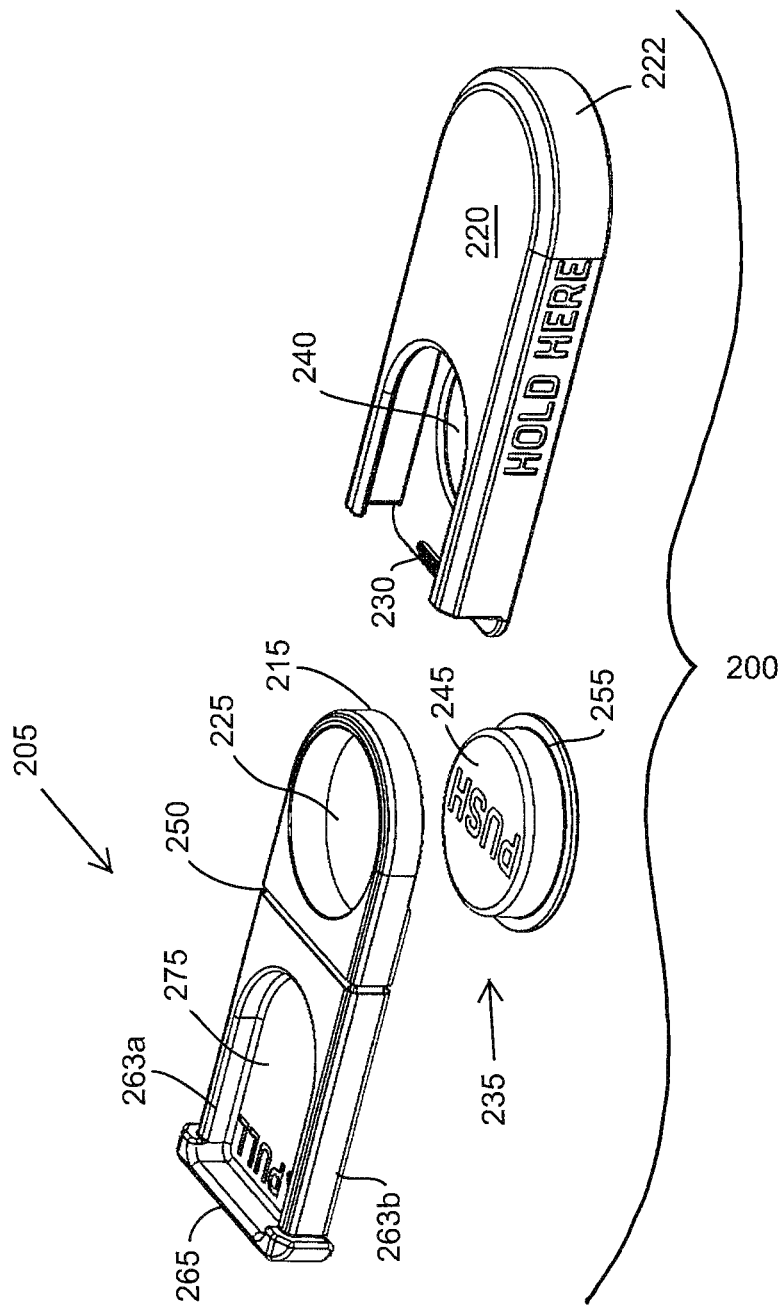
Figure 6C:
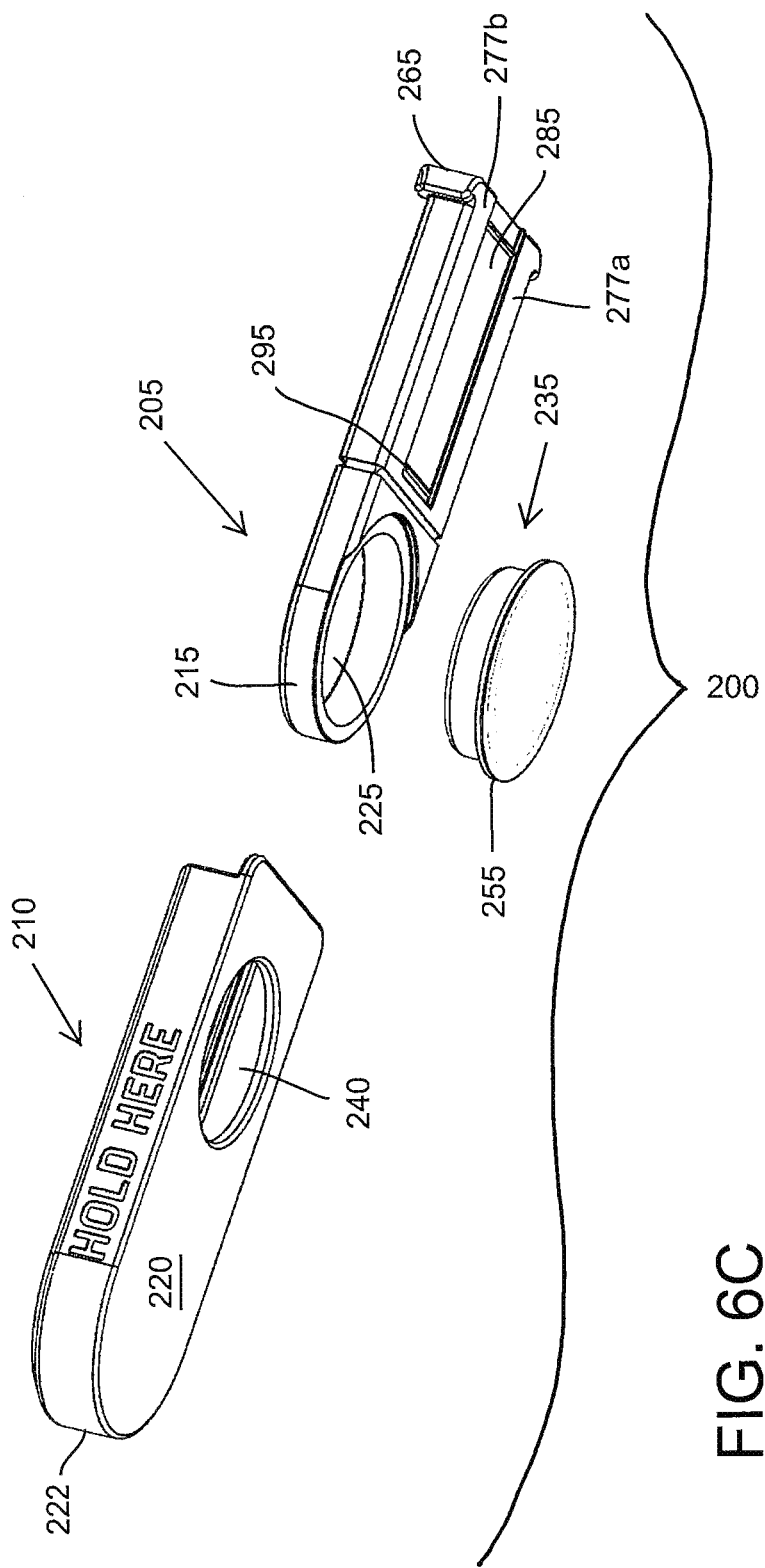

FIGS. 6A, 6B and 6C illustrate another embodiment of a portable medicament case 200 which has an elongated housing resembling a military dogtag. The first housing member 205 is configured as an elongated male slide member having a forward end 215 that includes aperture 225 therein for receiving and snugly maintaining the medicament package, while the second housing member 210 is an elongated female member having a rearward end 222 that forms a closed cavity 220 that is configured for receiving the forward end 215 and aperture 225 of the male slide member therein.

The first housing member has a rearward end that includes a grasping portion 265 for withdrawing the first housing member 205 from the cavity 220 or the second housing member 210. While the forward end 215 needs to have aperture 225 to receive medicament package 235, the rearward end of the first housing member can either be solid or can at least have an opening 275 to reduce the weight of the first housing. The grasping portion 265 preferably includes arm members 263a, 263b that are attached to the rearward end of the first housing member 205. These arm members are attached at a lower portion by floor portions 277a, 277b. The rearward end of the first housing member may also be marked with indicia (such as PULL with an arrow) to indicate which way to withdraw the first housing member from the second housing member.

The lower wall member of the rearward portion of the first housing member preferably includes a slot 285 and a terminal barrier 295 at a forward end of the slot. Also, the rearward end of the second housing member includes a protrusion 230 that is surrounded by the slot as the first housing member is withdrawn from the cavity 220 of the second housing member. To prevent disconnection of the housing members, the terminal barrier 295 at the forward end of the slot 285 contacts the protrusion 230.

The second housing member lower wall includes a rearward end that has an opening 240 such that when the slide member is withdrawn from the cavity and placed over that opening, the medicament package 235 can be removed by depressing an upper portion of the medicament package 245 using finger force to push the medicament package out of aperture 225 and then through aperture 240 to remove the medicament package from the case. And while the case is typically discarded, in some situations it can be re-used and preventing complete disengagement of the first housing member from the second housing member facilitates recycling and reuse of the case. The first and second housing members can be made of a plastic, elastomeric or metal material, with aluminum being preferred.

To maintain the medicament package sealed in the case, first housing member 205 can preferably include a protruding portion or gasket 250 around a central portion of the housing member. This protrusion or gasket 250 forms a seal when inserted into the second housing member 210 so that the medicament package does not is not contacted by moisture or other contaminants when stored in the case.

The second housing member 210 has a closed forward and 220 so that the medicament package 235 is securely received therein. As noted, protrusion or gasket 250 on the first housing 205 forms a seal with the inner walls of second housing member 210. The second housing member also has an indicia such as HOLD HERE to indicate where the user should grasp the second housing member when the first housing member is to be removed therefrom.

The invention also relates to a magazine comprising a supporting member such as a strap, rod or chamber and a plurality of portable medicament cases comprising first and second housing members that are configured to form a medicament package receiving cavity when joined together, with each housing member including a mating member that is configured for engagement with the other housing member in order to join the first and second housing members together in a manner that prevents moisture or contaminants from entering into the cavity. Each also contains a medicament provided in a package. To remove the package from the medicament case, the housing members are movable relative to each other to provide access to the medicament package when needed and the plurality of medicament cases facilitate distribution to multiple persons in need of the medicament.

The supporting member generally has associated therewith or connected thereto a plurality of base members, and each portable medicament case is operatively associated with and removably connected to the base members to provide the plurality of medicament cases for distribution of the medicament. The first and second housing members are preferably configured to form a medicament package receiving cavity when joined together, with each housing member including a mating member that is configured for engagement with the other housing member in order to join the first and second housing members together.

In a preferred arrangement, the first housing member includes an exterior surface exposed to the environment and an interior surface facing the package, the interior surface defining an aperture and includes an adhering member for retaining the package is located in the interior surface of the first housing member; and an ejection button configured to disengage the package from the first housing member upon depression by application of finger force that overcomes the adhering member when the first housing member is not connected in mating engagement with the second housing member.

The portable medicament cases can further comprise an outer housing having a cavity that is configured and dimensioned to receive a plurality of portable medicament cases therein in a stacked vertical orientation, the housing including a side opening that allows a single medicament case to be removed at a time; and biasing means that urges the medicament cases towards the side opening such that once one case is removed another is urged into position for removal. The side opening is typically provided in an uppermost location of the housing and the biasing means comprises a spring that is provided in a lowermost location in the housing cavity, with the spring configured to urge each medicament case towards the opening for individual removal. The magazine can include openings or windows in the housing positioned adjacent each case to allow a user to visually determine whether a case has been dispensed from the magazine and to determine if additional cases remain for further dispensing. Preferably, the magazine includes between 10 and 25, between 10 and 50 or even between 10 and 100 medicament cases or more.

In another embodiment, the invention relates to a method of administering medications to mass casualties of multiple persons that are in need thereof. The method comprises providing a magazine of portable medicament cases as disclosed herein. Each of the cases comprises an outer housing having a cavity that is configured and dimensioned to receive a medicament therein, wherein the medicament comprises an oral composition that comprises at least one active pharmaceutical ingredient in a therapeutically effective amount and at least one dye in an effective amount to stain a person's mouth as an identification of consuming the oral composition. The magazine facilitates rapid dispensing of the oral composition to persons of the mass casualties for consumption thereof. A determination of who received the medication and who did not is provided simply by visually observing the person's mouth for staining by the dye.

The dye is present to provide a stain having a red, yellow, orange, green, blue, purple or black color with the color used as an indication of the type of medicament that is distributed such that a simple viewing of the person's mouth also readily identifies whether the person consumed the correct medicament or not. The mass casualties include military personnel who participated in a battle or conflict, civilian personnel that were subject to an act of terrorism, or person who were subjected to a natural disaster with the color of the stain from the dye indicating the active pharmaceutical ingredient of the medicament that was administered. The doses of the oral compositions to be administered are sealed in the medicament package to avoid contact with moisture prior to consumption. Also, the medicament is also formulated with one or more disintegrating agents configured to rapidly disintegrate when placed in a person's mouth to quickly introduce the medicament into the person.

The use of a dye in the medicament or pharmaceutical will stain the person's mouth when consumed to provide a clear and visible indication that the medicament or pharmaceutical was administered. This can demonstrate quickly whether the person received treatment or not and is also an indicator to other medical personnel who may later treat the person or persons. The dye provided a quick visual indicator to medics as to who was treated (mouth is colored or stained) and who is left to be treated (no mouth stain). And after the injured are transported in an ambulance or helicopter, different medical transport personnel will be involved and they can also easily determine whether the persons have been treated. The same is true once the injured arrive at a hospital. The color indicates that the person has been treated so that even if the injured person is now unconscious, the doctors can understand what they have taken before doing surgeries or other procedures.

The medicaments can be identified in the medicament package by the use of various codes alone or in combination with an indication of the dye color. This is also helpful in insuring that the medic is distributing the correct drug by comparing the color of the mouth stain with the package indication. And while there are not enough different discernable colors to code each type of drug, certain classes of drugs that would be used in particular situations would be generally understood. For example, in a military battle where nerve gas is involved, the counteracting drugs can have one color while pain killer medication can have another color. Also, the coloring of certain drugs (e.g., narcotics) could also be used to prevent abuse such as to prevent overdosing where the person says he was not treated but the coloration of his mouth is evidence that he was already treated.

Thus, the oral compositions that are provided in the medicament package generally comprises at least one active pharmaceutical ingredient in a therapeutically effective amount and at least one dye in an effective amount to stain a person's mouth as an identification of consuming the oral composition, in order to identify the consumed dosage of the medication, to reduce confusion when the person is later inspect by a medical professional, and to safeguard against overdoses or abuse of medications.

In one aspect of the present application, the oral composition is in a tablet or wafer dosage form comprising one or more appropriate excipients or diluents formulated with the active pharmaceutical ingredient and the dye to form the tablet or wafer. The oral composition is formulated to rapidly disintegrate in the person's mouth, wherein the oral composition comprises one or more disintegrating agents to facilitate dissolution in the person's mouth. In one aspect of the present application, the oral composition is formulated to dissolve in the person's mouth in less than 45 seconds.

In one aspect, the medication is orally administrated through sublingual route in the dosage form of a tablet or wafer, such as oral disintegrating tablets (ODT) or rapid dissolve tablet (RDT), with instant dissolution to release the pharmaceutical active ingredient to blood stream through sublingual route. The tablet or wafer will be quickly dissolved beneath the tongue in the buccal cavity or in the mouth. Following sublingual administration, the medication is expected to be released for rapid diffusion through the epithelium and to be absorbed into venous circulation through a diffusion process via crossing the connective tissue and highly profused capillaries.

In one aspect of the present application, the rapidly disintegrating tablet or wafer is formulated in the fast-disintegrating dosage forms as described in U.S. Pat. No. 5,576,014 (Mizumoto et al., published on Nov. 19, 1996, Intrabuccally dissolving compressed moldings and production process thereof) and Liang (Expert Opinion in Therapeutic Patents, 11(6), 981-986, 2001, by Liang and Chen), which are incorporated herein as references in their entirety. Mizumoto et al. discloses an intrabuccally dissolving compressed molding comprising a saccharide having low moldability (such as lactose, mannitol, glucose, sucrose, and xylitol) having been granulated with a saccharide having high moldability (such as maltose, maltitol, sorbitol and an oligosaccharide).

A flash-melt pharmaceutical oral dosage form described in US 2002/0076437 A1 (Kothari et al, published on Jun. 20, 2002, Flash-melt oral dosage formulation) is incorporated herein as references in its entirety, which discloses a medicament comprising the granules that are composed of an excipient combination consisting of a super-disintegrant (such as low-substituted hydroxypropyl cellulose, or pregelatinized starch), a dispersing agent (such as calcium silicate, magnesium trisilicate, or silicic acid), a distributing agent (such as silica, talc, or diatomaceous earth), and a binder (such as microcrystalline cellulose, hydroxypropyl cellulose, ethyl cellulose, lactose, mannitol, or calcium phosphate).

Platteeuw et al. (US 2004/0265375 A1, published on Dec. 30, 2004, Orally disintegrating tablets) discloses a silicified microcrystalline cellulose as a component to formulate a tablet in orally fast-disintegrating dosage form, which is incorporated herein by reference in its entirety.

In one aspect of the present application, the rapidly disintegrating tablet or wafer is formulated in the fast-disintegrating dosage forms as described in Venkatesh et al. (US 2005/0232988 A1, published on Oct. 20, 2005, Orally disintegrating tablets and methods of manufacture) and Blank et al. (U.S. Pat. No. 4,946,684, published on Aug. 7, 1990, Fast dissolving dosage forms), which are incorporated herein as references in their entirety. Venkatesh et al. discloses a blend of rapidly dispersing microgranules prepared by granulating a sugar alcohol or a saccharide or a mixture thereof and a disintegrant. Blank et al. discloses a fast-disintegrating dosage form having an open matrix network structure comprising a mannitol and a natural gum.

The dye of the oral composition is formulated to temporarily stain at least the person's tongue and mouth and optionally stain the person's teeth and lips upon consumption of the oral composition, when the oral composition contacts with the person's saliva. The active pharmaceutical ingredient of the present application is designed to counteract an injury suffered by the person. The active pharmaceutical ingredient may include an analgesic agent, a sedative, an antibiotic, or an antidote to a chemical agent. For example, when the chemical agent is a nerve agent selected from the group consisting of soman, sarin, tabun, cyclosarin, GV, a novichock agent, EA-3148, VE, VG, VM, VP, VR, VX, Trilon-83, or saxitoxin, the antidote would be selected from the group consisting of atropine sulfate, 2-PAM, diazepam, procyclidine, and a combination thereof.

The dye of the oral composition of the present application provides a stain having a red, yellow, orange, green, blue, purple or black color when the oral composition is consumed such that a simple viewing of the person's mouth readily identifies whether the person consumed the medication or not. In one aspect, the dye of the present application may include various dyes, such as FD&C dyes or natural coloring agents. Gruber (U.S. Pat. No. 7,214,385 B2, published on May 8, 2007, Pharmaceutical formulation containing dye) discloses various dyes to be incorporated into pharmaceutical formulations as aversion agents to deter an abuser from administering a tempered dosage form, which is incorporated herein by reference in its entirety. Chang et al. (U.S. Pat. No. 8,906,413 B2, published on Dec. 9, 2014, Drug formulations having reduced abuse potential) discloses drug formulations having reduced abuse potential containing a bright deterrent/indicator dye, which is incorporated herein as references in its entirety.

In one aspect, the present application provides a method of administering medications to mass casualties of multiple persons that are in need thereof, which comprises: dispensing the oral composition to persons of the mass casualties for consumption thereof; and determining which persons have consumed the oral composition by observing staining of the persons' mouths with the dye, wherein the mass casualties include military personnel who participated in a battle or conflict, civilian personnel that were subject to an act of terrorism, or person who were subjected to a natural disaster, wherein the color of the stain from the dye indicates what type of the active pharmaceutical ingredient was administered.

In one aspect, the oral composition is dispensed from a magazine that holds multiple oral compositions and that can readily dispense single doses of the oral composition from the magazine, wherein the magazine includes between 10 and 25 doses of oral compositions and has openings to determine whether additional oral composition is present in the magazine for dispensing, wherein the doses of the oral compositions to be administered are sealed in a package to avoid contact with moisture prior to consumption.

Figure 7A:
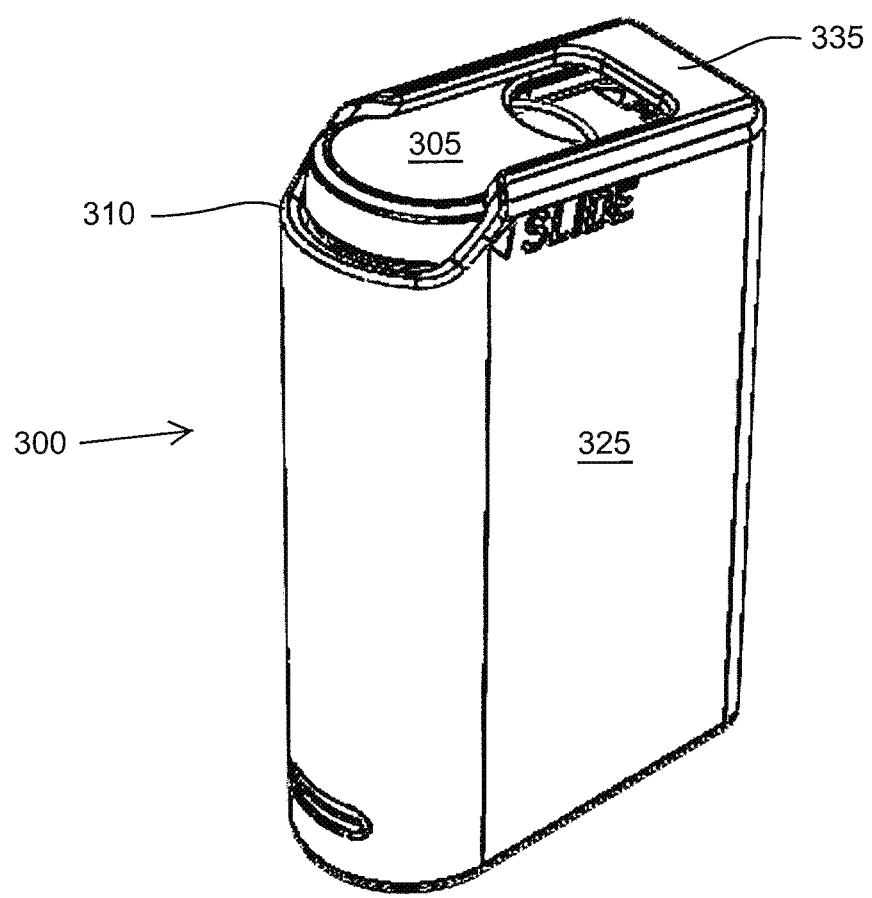
FIGS. 7A and 7B are front and rear perspective views of a magazine for holding a plurality of medicament cases according to FIGS. 6A, 6B and 6C.
Figure 7B:
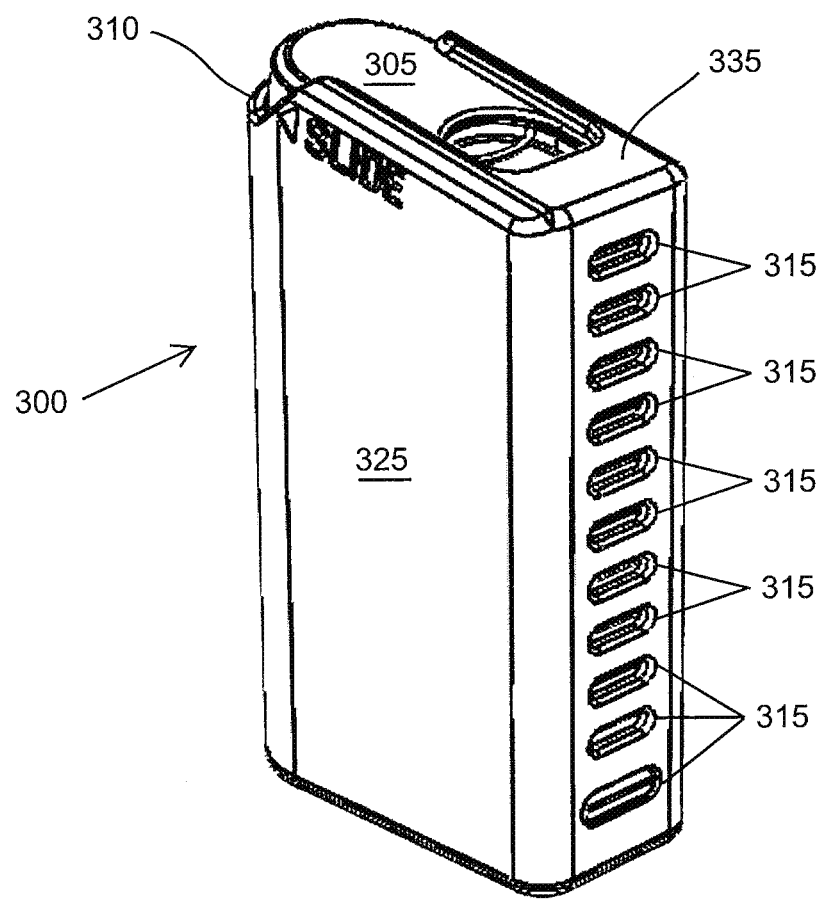

FIGS. 7A and 7B depict a magazine 300 that is used to retain a plurality of portable medicament cases according to FIGS. 6A, 6B and 6C. The magazine 300 is configured with a cross-sectional shape that is slightly larger than the shape of the portable medicament cases so that they can be stacked and placed inside of the magazine. One case can be viewed at the top of the device near an open notch 310. To remove the case from the magazine, the user can simply slides the case 305 from the retaining shoulder 335 towards the forward end of the device through slot 310. The magazine may also include indicia such as the word SLIDE and an arrow to show the direction that the case must be moved to provide access to the medicament package 235 from the magazine.

As shown in FIG. 7B, the rear portion of the magazine has a plurality of windows 315 which allow viewing of the interior of the magazine to determine how many medicament cases remain available for use. As shown in the drawing 11 windows are provided one for each case that is housed in the magazine for dispensing so that the person dispensing the cases will know exactly how many cases remain by simple visual observation.

Figure 8A:
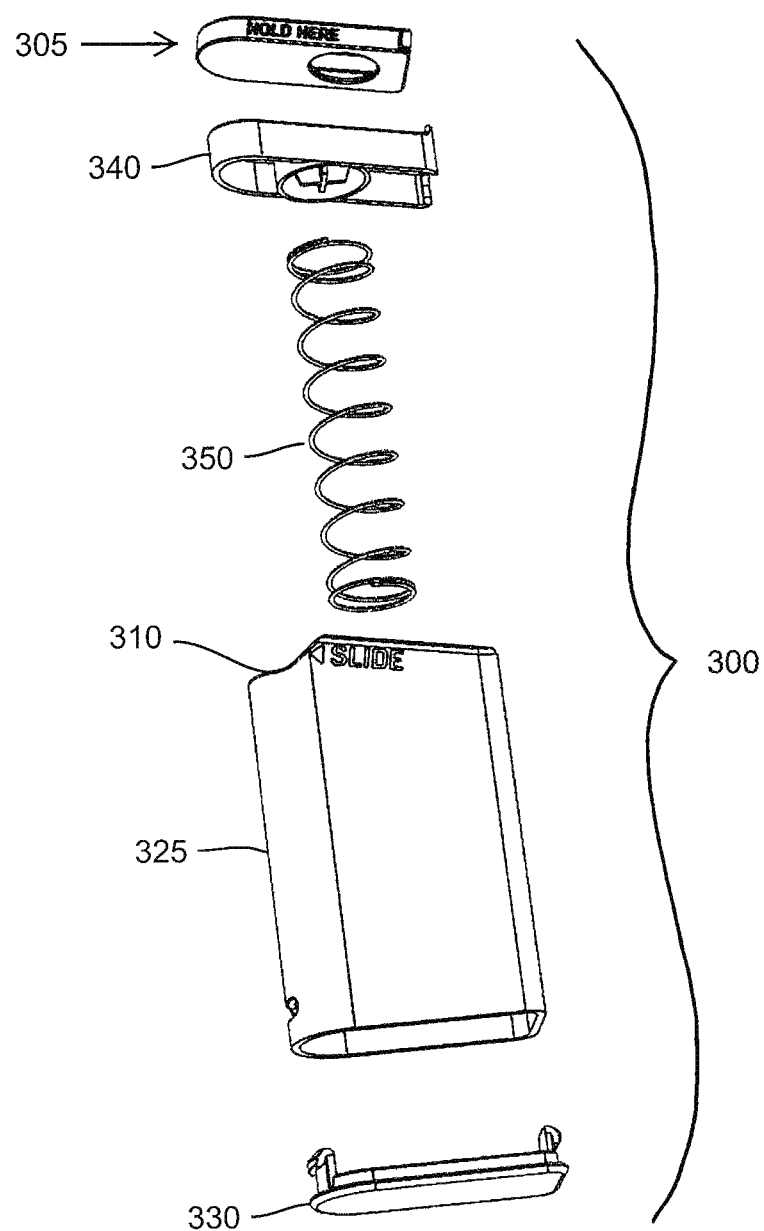
FIGS. 8A and 8B are bottom-up and top-down exploded perspective views, respectively, of the magazine of FIGS. 7A and 7B.
Figure 8B:
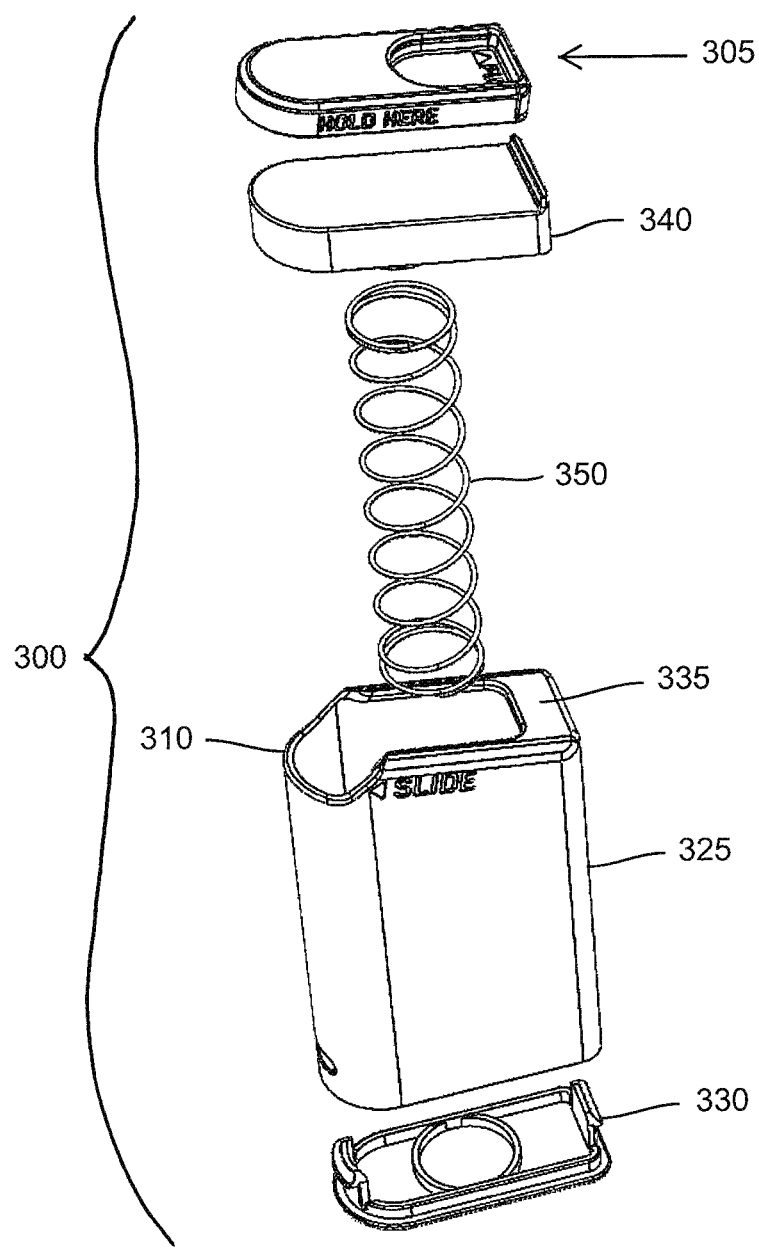

FIGS. 8A and 8B are exploded views of the magazine 300 to illustrate the various components of the magazine. As shown, the housing 325 includes a base 330 that is clipped on to the bottom of the housing 325. A platform 340 is associated with the coil spring 350 to provide a bias in the upward direction so that the platform 340 can urge each medicament case 305 towards the top of the device for removal through slot 310. To prevent the spring and platform from pushing the cases out of the housing, retaining shoulder 335 is provided. Thus, as the uppermost case is removed from the magazine, the subjacent case is urged upward into position for removal. This continues until all of the cases present in the magazine are dispensed.

Figure 9A:
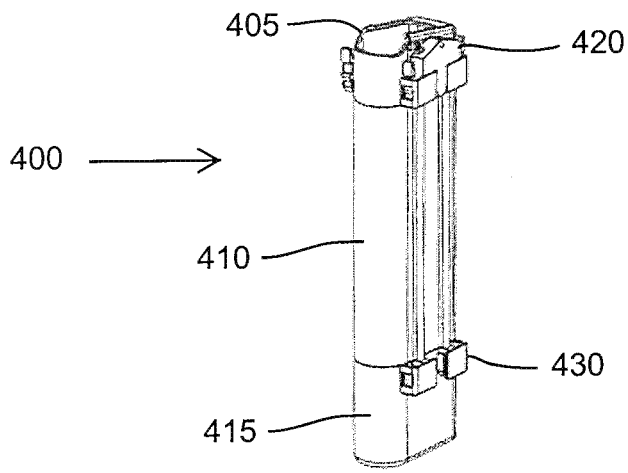
FIGS. 9A, 9B and 9C are front, rear and exploded perspective views of a magazine for holding a plurality of medicament cases according to another embodiment of the invention.
Figure 9B:
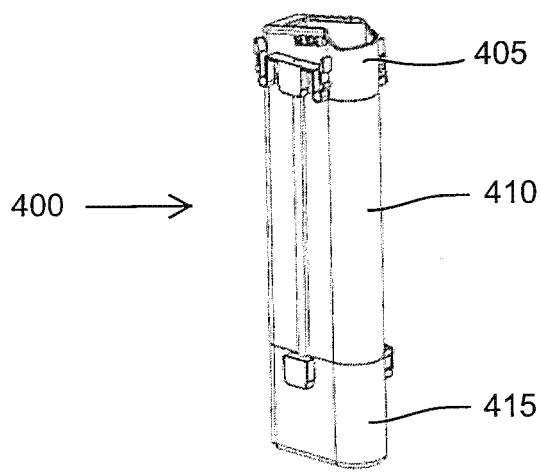
Figure 9C:
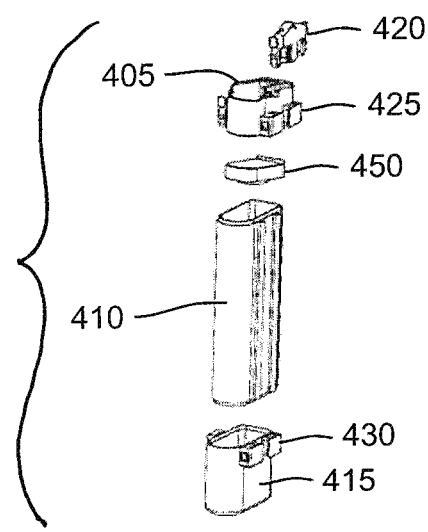

FIGS. 9A, 9B and 9C are views of another magazine 400 according to the present invention. This magazine 400 is configured similar to magazine 300 of FIGS. 7A, 7B, 8A with a cross-sectional shape that is slightly larger than the shape of the portable medicament cases that are stacked and placed inside of the magazine 400.

The magazine 400 includes a top portion 405, housing 410 and base portion 415 that are connected together by molle clip 420 and connectors 425, 430. The medicament cases sit on a platform 450 which is supported by a coil spring as shown in the preceding embodiment to provide a bias in the upward direction so that the platform 450 can urge each medicament case towards the top of the device for removal through a slot. To prevent the spring and platform from pushing the cases out of the housing, a retaining shoulder is provided in the top portion 405. Thus, as the uppermost case is removed from the magazine, the next case is urged upward into position for removal. This continues until all of the cases present in the magazine are dispensed.

EXAMPLES

The following examples illustrate the advantages and unexpected results that are provided by the present invention.

Example 1

An individual who is a tactical paramedic tested the device of FIG. 1. The individual had sustained an injury that left him with subsequent seizures. The individual wore the device with anti-epileptic medication stored in it. The individual had a medical emergency one evening when he went into status epilepticus, a life threatening medical condition. The individual had several hours of waxing and waning consciousness. During a period of consciousness the individual was able to deploy the device secured to his wrist and take the medication that ultimately stopped his status epilepticus. It was several hours before he was found in a postictal state at the bottom of the stairs. The individual reports that he would not have been able to get to the kitchen in order to get his medication, however since the medication was maintained in the pod on his wrist he was able to give himself the medication.

This demonstrates certain additional uses of the invention beyond military applications. There are multiple medical conditions in which a civilian individual can deploy the device for taking life-saving medication or for providing immediate comfort. Additional examples would be pods provided with nitroglycerine for CP, Zofran for CA patients, or Glucose for DM.

Example 2

Two individuals were asked to wear the device and attempt to deploy the device in order to provide feedback on usability, wearability, and durability during a tactical medical obstacle course that spanned the course of several days. The individuals reported that the device is easily worn in similar fashion to a watch. Weight is not a factor and the size is similar to that of a watch and was not a hindrance. As there is no metal on the back of the device, one individual found that to be an advantage as he is allergic to nickel. The pod was easily deployed with fingers only during the beginning of the exercise, however after several hours this became more difficult and deploying the device using an open palm was found to be easier. This was slightly more difficult while wearing thick leather gloves, but it only required a few seconds more to deploy.

Example 3

One individual was asked to utilize the device during tactical range exercises under stress. The individual attempted multiple deployments with the device during tactical stress shooting which included exercises of physical exercises followed by shooting as well as the removal of fine motor skills during the tactical exercises by methods such as icing the hands for 90 seconds prior to deployment of the device in order to simulate a tactical situation. The individual found that the deployment of the device using his fingers/fine motor skills was rather difficult but that using the palm of the hand was much easier. Using gloved hands in order to deploy the device was more cumbersome yet still manageable. The device did not impede tactical operations. The device did not require moving other wrist devices and placing them elsewhere.

Example 4

The inventor has carried and worn the device in multiple settings. The deployment of the device has been easy without difficulties. The corners have been rounded enough that it no longer snags or catches on clothes or other equipment. The band is comfortable to wear and has a low profile. The device takes less than 5 seconds to deploy and access the medicament.

Example 5

In a tactical setting in order to medicate a soldier, a medic or combat life saver takes several minutes before being able to administer any medications. First, a soldier must be beyond the care under fire phase and moved onto the tactical field care. A primary survey must be completed and then IV access must be established prior to administration. In contrast, the orally disintegrating tablets of the invention are easy to withdraw from the pod and after administration immediately release the medicament.

Example 6

In the situation where a soldier is wounded on the battlefield and is given a particular medication that would have the soldier's mouth stained blue once the specific medication is taken. The battlefield medic and the soldiers handling the transfer-to-helicopter, and transfer-to-hospital all have immediate and accurate knowledge of what that soldier has taken. And in the situation where a number of soldiers are subject to a chemical attack, the particular counteracting medicament that is administered that includes the dye-system would assist in clearly showing who had and had not taken medication. EMTs and other emergency personnel could easily access the situation more effectively seeing who needs the immediate assistance while also avoiding the administration of a second or double-doses.

Example 7: Dosages of Antidotes of Organophosphate Nerve Agents

Organophosphate nerve agents exert a variety of toxicological effects as they target multiple organs and systems in the body. Out of all the signs and symptoms, seizure activity is the most serious and life-threatening. Several neurotransmitters are involved sequentially in the initiation, progression and maintenance of seizures. Progression of such events takes place in three phases (three-phase model):

Phase-1: Early cholinergic phase is from the time of exposure to 5 min after onset of seizures which is dominated by cholinergic activity. In addition to seizures, due to hyper stimulation of muscarinic acetylcholine receptors, excessive secretions, such as salivation, lacrimation, urination, and diarrhea are evident.

Phase-2: Transitional phase of cholinergic and glutamatergic hyperactivity.

Phase-3: Predominantly glutamatergic phase after approximately 40 min of seizures onset.

According to this three phase model, efficacious pharmacological countermeasures against nerve agents should preferentially exert cholinergic and glutamatergic antagonism along with gamma aminobutyric acid agonism.

The dosages of the active pharmaceutical ingredient of the oral composition comprise:

1. Atropine sulfate (2 mg): muscarinic acetylcholine receptor blocker to prevent or stop salivation, lacrimation, urination, and diarrhea.

2. 2-PAM (1800 mg): acetylcholinesterase reactivator to restore normal acetylcholine hydrolysis.

3. Procyclidine (5 mg): N-methyl-D-aspartate receptor antagonist to inhibit the phencyclidine site at N-methyl-D-aspartate receptor to prevent or antagonize seizures. Alternatively, another N-methyl-D-aspartate receptor antagonist memantine at 5-10 mg can be used.

4. Diazepam (5 mg): it exerts anti-seizure and muscle relaxant activities.

The administration of antidotes (atropine sulfate+2-PAM+procyclidine+diazepam) by sublingual route can provide optimal protection or countermeasure against the toxic effects of organophosphate nerve agents.

Example 8: Oral Compositions with Acidic pH

With sublingual administration, some antidotes of nerve agents may face the degradation by salivary enzymes (mainly amylase). Since the pH of saliva remains in the range of pH 6.75-7, the oral composition in the tablet or wafer is formulated to acidic pH by adding citrate buffer.

It is to be understood that the present invention is not to be limited to the exact description and embodiments as illustrated and described herein. To those of ordinary skill in the art, one or more variations and modifications will be understood to be contemplated from the present disclosure. Accordingly, all expedient modifications readily attainable by one of ordinary skill in the art from the disclosure set forth herein, or by routine experimentation therefrom, are deemed to be within the true spirit and scope of the invention as defined by the appended claims.

What is claimed is:

1. A portable medicament case comprising:
a medicament provided in a package;

first and second housing members that are configured to form a medicament package receiving cavity when joined together, with each housing member including a mating member that is configured for engagement with the other housing member in order to join the first and second housing members together in a sealed configuration that prevents moisture or contaminants from entering into the cavity;

a gasket removably positioned between the first and second housing members to provide a hermetic seal about the medicament package when the housing members are in the mating engagement in the sealed configuration; and a base member configured to selectively receive the second housing member opposite the first housing member, the base member including a means for connection that forms or is connectable to a rod, strap, belt or clothing article for secure transport of the portable medicament case on or with a person;

wherein one housing member includes an aperture configured to assist in removing the medicament package from that housing member when the housing members are not joined together in the sealed configuration.

2. The portable medicament case of claim 1, wherein the medicament package is a blister pack that is sealed to further prevent moisture from contacting the medicament.

3. The portable medicament case of claim 1, wherein a lower portion of
the second housing member has a ramp member that has angled sidewalls and an upper portion of the base member has a slot with angled sidewalls that are complimentary to those of the ramp member so that the ramp member can be slid into and securely received by the slot.

4. The portable medicament case of claim 1, wherein the medicament: (a) comprises an oral composition that comprises at least one active pharmaceutical ingredient in a therapeutically effective amount and at least one dye in an effective amount to stain a person's mouth as an identification of consuming the oral composition, (b) is formulated with one or more disintegrating agents configured to rapidly disintegrate when placed in a person's mouth, or (c) includes both (a) and (b).

5. The portable medicament case of claim 4, wherein the medicament is in a tablet or wafer dosage form comprising one or more appropriate excipients or diluents formulated with the active pharmaceutical ingredient and the dye.

6. The portable medicament case of claim 5, wherein the medicament includes sufficient dye to temporarily stain at least the person's tongue and mouth and optionally stain the person's teeth and lips upon consumption of the oral composition when the oral composition contacts the person's saliva.

7. The portable medicament case of claim 4, wherein the medicament is formulated to dissolve in the person's mouth in less than 45 seconds, less than 30 seconds, or less than 15 seconds.

8. The portable medicament case of claim 4, wherein the medicament comprises an analgesic agent, a sedative, an antibiotic, or an antidote to a chemical agent.

9. The portable medicament case of claim 1, wherein the means for connection comprises a pair of L-shaped members that face each other and that form an opening to receive a strap or band therein.

10. The portable medicament case of claim 2, wherein the blister package includes indicia to indicate where force is to be applied to remove the medicament.

11. A portable medicament case comprising:
a medicament provided in a package;
first and second housing members that are configured to form a medicament package receiving cavity when joined together, with each housing member including a mating member that is configured for engagement with the other housing member in order to join the first and second housing members together in a sealed configuration that prevents moisture or contaminants from entering into the cavity;

a gasket removably positioned between the first and second housing members to provide a hermetic seal about the medicament package when the housing members are in the mating engagement in the sealed configuration;

a base member configured to selectively receive the second housing member opposite the first housing member; and an ejection button having a shape and dimension that conforms to that of the aperture of the first housing member;

wherein one housing member includes an aperture configured to assist in removing the medicament package from that housing member when the housing members are not joined together in the sealed configuration;

further wherein each of the ejection button and the aperture having a thickness and parameter that provides a snug fit of the ejection button in the first housing aperture but allows depression of the ejection button by finger force into the cavity.

12. The portable medicament case of claim 11, further comprising a flange to assist in seating the medicament package beneath the button.

13. The portable medicament case of claim 11, wherein the medicament package is a blister pack that is sealed to further prevent moisture from contacting the medicament.

14. The portable medicament case of claim 13, wherein the blister package includes indicia to indicate where force is to be applied to remove the medicament.

15. The portable medicament case of claim 11, wherein the medicament: (a) comprises an oral composition that comprises at least one active pharmaceutical ingredient in a therapeutically effective amount and at least one dye in an effective amount to stain a person's mouth as an identification of consuming the oral composition, (b) is formulated with one or more disintegrating agents configured to rapidly disintegrate when placed in a person's mouth, or (c) includes both (a) and (b).

16. A portable medicament case comprising:
a medicament provided in a package;
first and second housing members that are configured to form a medicament package receiving cavity when joined together, with each housing member including a mating member that is configured for engagement with the other housing member in order to join the first and second housing members together in a sealed configuration that prevents moisture or contaminants from entering into the cavity;

a gasket removably positioned between the first and second housing members to provide a hermetic seal about the medicament package when the housing members are in the mating engagement in the sealed configuration;

a base member configured to selectively receive the second housing member opposite the first housing member;

wherein one housing member includes an aperture configured to assist in removing the medicament package from that housing member when the housing members are not joined together in the sealed configuration;

further wherein the mating members comprise threads that are engaged by screwing the first housing member onto the second housing member, and wherein the first housing member further comprises opening members configured as a wall member that protrudes from a floor of the first housing member and that is engageable by a user's hand to provide a twisting force to the first housing member for disengagement from the second housing member.

17. The portable medicament case of claim 16, wherein the opening members are operatively associated with the threaded mating members to allow rotation of the first housing member in only one rotation direction.

18. The portable medicament case of claim 16, wherein the medicament package is a blister pack that is sealed to further prevent moisture from contacting the medicament.

19. The portable medicament case of claim 18, wherein the blister package includes indicia to indicate where force is to be applied to remove the medicament.

20. The portable medicament case of claim 16, wherein the medicament: (a) comprises an oral composition that comprises at least one active pharmaceutical ingredient in a therapeutically effective amount and at least one dye in an effective amount to stain a person's mouth as an identification of consuming the oral composition, (b) is formulated with one or more disintegrating agents configured to rapidly disintegrate when placed in a person's mouth, or (c) includes both (a) and (b).

* * * * *